US008920813B2

(12) United States Patent
Bruder et al.

(10) Patent No.: US 8,920,813 B2
(45) Date of Patent: Dec. 30, 2014

(54) ADENOVIRAL VECTOR-BASED DENGUE FEVER VACCINE

(75) Inventors: Joseph T. Bruder, Gaithersburg, MD (US); Duncan McVey, Derwood, MD (US); Douglas E. Brough, Gaithersburg, MD (US)

(73) Assignee: GenVec, Inc., Gaithersburg, MD (US)

(*) Notice: Subject to any disclaimer, the term of this patent is extended or adjusted under 35 U.S.C. 154(b) by 0 days.

(21) Appl. No.: 13/993,210

(22) PCT Filed: Dec. 20, 2011

(86) PCT No.: PCT/US2011/066030
§ 371 (c)(1), (2), (4) Date: Jun. 20, 2013

(87) PCT Pub. No.: WO2012/088041
PCT Pub. Date: Jun. 28, 2012

(65) Prior Publication Data

US 2013/0337008 A1 Dec. 19, 2013

Related U.S. Application Data

(60) Provisional application No. 61/425,092, filed on Dec. 20, 2010.

(51) Int. Cl.

| | |
|---|---|
| ***A61K 39/12*** | (2006.01) |
| ***C07K 14/005*** | (2006.01) |
| ***C12N 15/86*** | (2006.01) |
| ***C12N 15/63*** | (2006.01) |
| ***C07H 21/04*** | (2006.01) |
| *A61K 39/00* | (2006.01) |

(52) U.S. Cl.
CPC ......... *A61K 39/12* (2013.01); *C12N 2810/6018* (2013.01); *A61K 2039/5256* (2013.01); *C07K 2319/00* (2013.01); *C07K 14/005* (2013.01); *C12N 2710/10322* (2013.01); *C12N 2770/24134* (2013.01); *C12N 2710/10345* (2013.01); *C12N 2710/10343* (2013.01); *C07K 2319/40* (2013.01); *C12N 15/86* (2013.01)
USPC .................. 424/218.1; 424/184.1; 424/204.1; 424/233.1; 435/320.1; 435/395; 435/235.1

(58) Field of Classification Search
CPC ............ A61K 39/12; A61K 2039/525; A61K 2039/5258; A61K 35/76; A61K 39/295; C07K 14/005; C07K 2319/00; C12N 7/00; C12N 15/86; C12N 2770/24134; C12N 2015/00; C12N 2710/00; C12N 2710/00011; C12N 2710/10032; C12N 2710/10041
See application file for complete search history.

(56) References Cited

U.S. PATENT DOCUMENTS

| | | | | |
|---|---|---|---|---|
| 6,127,525 | A | 10/2000 | Crystal et al. | |
| 7,718,359 | B2 | 5/2010 | Guy et al. | |
| 2001/0026794 | A1* | 10/2001 | Kovesdi et al. | 424/93.21 |
| 2002/0004040 | A1* | 1/2002 | Kovesdi et al. | 424/93.21 |
| 2002/0031831 | A1* | 3/2002 | Kovesdi et al. | 435/456 |
| 2002/0110545 | A1* | 8/2002 | Kovesdi et al. | 424/93.21 |
| 2008/0003236 | A1* | 1/2008 | King et al. | 424/192.1 |

FOREIGN PATENT DOCUMENTS

| | | | |
|---|---|---|---|
| WO | WO 2006/040330 | A2 | 4/2006 |
| WO | WO 2007/027860 | A2 | 3/2007 |

OTHER PUBLICATIONS

Khanam S, Pilankatta R, Khanna N, Swaminathan S. An adenovirus type 5 (AdV5) vector encoding an envelope domain III-based tetravalent antigen elicits immune responses against all four dengue viruses in the presence of prior AdV5 immunity. Vaccine. Oct. 9, 2009;27(43):6011-21. doi: 10.1016/j.vaccine.2009.07.073. Epub Aug. 7, 2009.*

Jiménez JA, Li X, Zhang YP, Bae KH, Mohammadi Y, Pandya P, Kao C, Gardner TA. Antitumor activity of Ad-IU2, a prostate-specific replication-competent adenovirus encoding the apoptosis inducer, TRAIL. Cancer Gene Ther. Mar. 2010;17(3):180-91. Epub Oct. 2, 2009.*

McVey D, Zuber M, Ettyreddy D, Reiter CD, Brough DE, Nabel GJ, King CR, Gall JG. Characterization of human adenovirus 35 and derivation of complex vectors. Virol J. Oct. 19, 2010;7:276.*

De Paula SO, Lima DM, de Oliveira França RF, Gomes-Ruiz AC, da Fonseca BA. A DNA vaccine candidate expressing dengue-3 virus prM and E proteins elicits neutralizing antibodies and protects mice against lethal challenge. Arch Virol. 2008;153(12):2215-23. doi: 10.1007/s00705-008-0250-3. Epub Nov. 12, 2008.*

Henn, MR, et. al. Dengue virus 1 isolate DENV-1/BR/BID-V2378/2001, complete genome. GenBank Acc. No. FJ850073. Dep. Mar. 31, 2009.*

Apt,D., Punnonen,J. and Brinkman,A. Synthetic construct chimeric Dengue envelope antigen 6E12 mRNA, partial cds. GenBank Acc. No. DQ158255. Dep. Mar. 23, 2006.*

(Continued)

*Primary Examiner* — Benjamin P Blumel
*Assistant Examiner* — Rachel Gill
(74) *Attorney, Agent, or Firm* — Leydig, Voit & Mayer, Ltd.

(57) ABSTRACT

The invention relates to a replication-deficient adenoviral vector comprising two or more nucleic acid sequences encoding Dengue virus antigens and a chimeric hexon protein. The chimeric hexon protein comprises a first portion and a second portion. The first portion comprises at least 10 contiguous amino acid residues from a first adenovirus serotype (e.g., serotype 5 adenovirus hexon protein), optionally with one amino acid substitution. The second portion comprises (a) at least one hypervariable region (HVR) of a hexon protein of an adenovirus of a second adenovirus serotype, or (b) at least one synthetic hypervariable region (HVR) that is not present in the hexon protein of the wild-type adenovirus of the first adenovirus serotype.

20 Claims, 1 Drawing Sheet

(56) References Cited

OTHER PUBLICATIONS

Christenbury,J.G., Aw,P.P., Ong,S.H., Schreiber,M.J., Bennett,S.N., Gubler,D.J., Vasudevan,S.G., Ooi,E.E. and Hibberd,M.L. polyprotein [Dengue virus 2]. GenBank Acc. No. ADK37484. Dep. Sep. 3, 2010.*

Wang,P., Geng,L., Qin,E., Yu,M. and Zhao,W. polyprotein precursor [Dengue virus 4]. GenBank Acc. No. AAG30148. Dep. May 14, 2001.*

Appanna et al., "Cross-Reactive T-Cell Responses to the Nonstructural Regions of Dengue Viruses among Dengue Fever and Dengue Hemorrhagic Fever Patients in Malaysia," *Clin. Vaccine Immunol.*, 14(8): 969-977 (2007).

Brough et al., "A Gene Transfer Vector-Cell Line System for Complete Functional Complementation of Adenovirus Early Regions E1 and E4," *Journal of Virology*, 70(9): 6497-6501 (1996).

Crawford-Miksza et al., "Analysis of 15 Adenovirus Hexon Proteins Reveals the Location and Structure of Seven Hypervariable Regions Containing Serotype-Specific Residues,"*Journal of Virology*, 70(3): 1836-1844 (1996).

Crill et al., "Humoral Immune Responses of Dengue Fever Patients Using Epitope-Specific Serotype-2 Virus-Like Particle Antigens," *PLoS One*, 4(4): 1-17 (2009).

Ebner et al., "Comparative Sequence Analysis of the Hexon Gene in the Entire Spectrum of Human Adenovirus Serotypes: Phylogenetic, Taxonomic, and Clinical Implications," *Journal of Virology*, 79(20): 12635-12642 (2005).

European Patent Office, International Preliminary Report on Patentability in International Patent Application No. PCT/US2011/066030, 6 pages (Jul. 4, 2013).

European Patent Office, International Search Report in International Patent Application No. PCT/US2011/066030, 6 pages (Mar. 21, 2012).

European Patent Office, Written Opinion in International Patent Application No. PCT/US2011/066030, 6 pages (Mar. 21, 2012).

Gall et al., "Construction and Characterization of Hexon-Chimeric Adenoviruses: Specification of Adenovirus Serotype," *J. Virol.*, 72: 10260-10264 (1998).

Guha-Sapir et al., "Dengue Fever: new paradigms for a changing epidemiology," *Emerging Themes in Epidemiology*, 2: 1-10 (2005).

Lasaro et al., "New Insights on Adenovirus as Vaccine Vectors," *Molecular Therapy: The Journal of the America Society of Gene Therapy*, 17(8): 1333-1339 (2009).

Mota et al., "Humanized Mice Show Clinical Signs of Dengue Fever according to Infecting Virus Genotype," *J. Virology*, 83 (17): 8638-8645 (2009).

Osatomi et al., "Complete Nucleotide Sequence of Dengue Type 3 Virus Genome RNA," *Virology*, 176: 643-647 (1990).

Raviprakash et al., "A Tetravalent Dengue Vaccine Based on a Complex Adenovirus Vector Provides Significant Protection in Rhesus Monkeys against all Four Serotypes of Dengue Virus," *Journal of Virology*, 82(14): 6927-6934 (2008).

Roberts et al., "Hexon-chimaeric adenovirus serotype 5 vectors circumvent pre-existing anti-vector immunity," *Nature: International Weekly Journal of Science*, 441(7090): 239-243 (2006).

Roy et al "Isolation and Characterization of Adenoviruses Persistently Shed from the Gastrointestinal Tract of Non-Human Primates," *PLoS Pathog.*, 5(7): e100050.Doi:10.1371/journal.ppat.1000503 (2009).

Rux et al., "Structural and Phylogenetic Analysis of Adenovirus Hexons by use of High-Resolution X-Ray Crystallographic, Molecular Modeling, and Sequence-Based Methods," *J. Virol.*, 77(17): 9553-9566 (2003).

Setoguchi et al., "Intraperitoneal In Vivo Gene Therapy to Deliver α1-Antitrypsin to the Systemic Circulation," *Am. J. Respir. Cell Mol. Bio.*, 10: 369-377 (1994).

Toulou et al., "Complete Genomic Sequence of a Dengue Type 2 Virus from the French West Indies," *Biochemical and Biophysical Research Communications*, 277: 89-92 (2000).

Webster et al., "Progress Towards a Dengue Vaccine," *Lancet*, 9(11): 678-687 (2009).

Whitehead et al., "Prospects for a Dengue Virus Vaccine," *Nature Reviews Microbiology*, 5: 518-528 (2007).

Yei et al., "In Vivo Evaluation of the Safety of the Adenovirus-Mediated Transfer of the Human Cystic Fibrosis Transmembrane Conductance Regulator cDNA to the Lung," *Human Gene Therapy*, 5: 731-744 (1994).

Zabner et al., "Safety and Efficacy of Repetitive Adenovirus-Mediated Transfer of Primates and Cotton Rats," *Nature Genetics*, 6: 75-83 (1994).

* cited by examiner

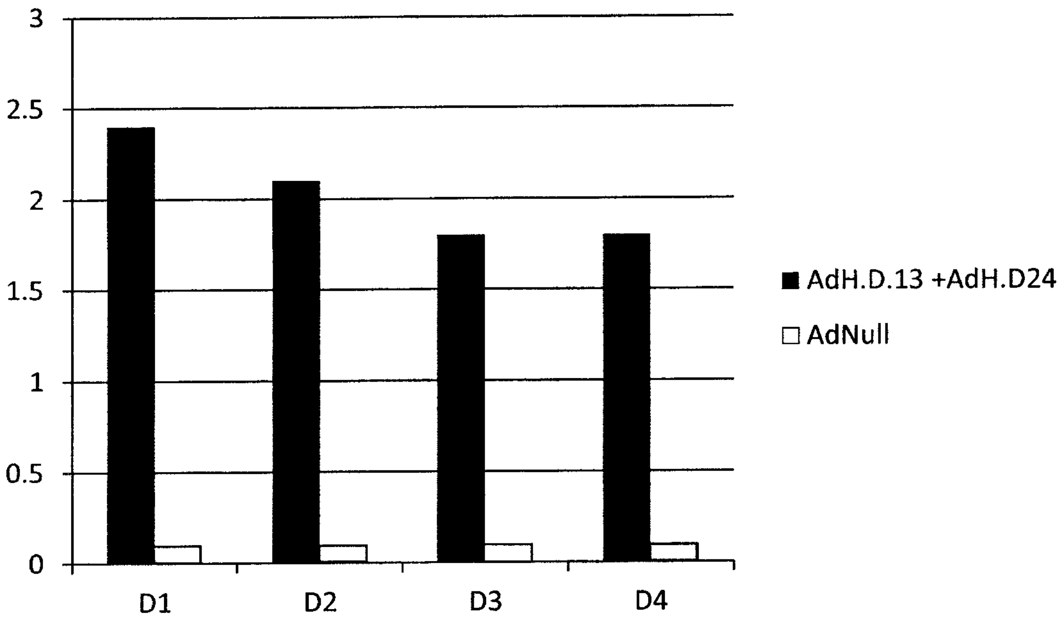
3
2.5
2
1.5
1
0.5
0
D1
D2
D3
D4
AdH.D.13 +AdH.D24
AdNull

ADENOVIRAL VECTOR-BASED DENGUE FEVER VACCINE

CROSS-REFERENCE TO RELATED APPLICATIONS

This patent application claims the benefit of U.S. Provisional Patent Application No. 61/425,092, filed Dec. 20, 2010, which is incorporated by reference.

STATEMENT REGARDING FEDERALLY SPONSORED RESEARCH AND DEVELOPMENT

This invention was made in part with Government support under National Institute of Allergy and Infectious Diseases (NIAID) grant number 1 R43 AI77309-01. The Government may have certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 60,213 bytes ASCII (text) file named "713667_ST25.txt," created on Jun. 7, 2013.

BACKGROUND OF THE INVENTION

Dengue fever and its more severe forms, Dengue hemorrhagic fever and Dengue shock syndrome, are the most prevalent vector-born viral diseases in humans. Dengue virus is typically found in tropical and subtropical regions. Over the course of the past fifty years, the Dengue virus has spread to more areas of the world and is now prevalent in over one hundred countries, including some parts of the United States. The World Health Organization (WHO) estimates that approximately 40% of the world's population, i.e., over 2.5 billion people, lives in areas at risk of Dengue infection, resulting in 100 million cases of Dengue fever and 500,000 cases of Dengue hemorrhagic fever annually. In addition to the residents of these countries, especially those who live in poverty, travelers and military personnel are at risk of exposure. A growing population, along with an increase in global travel and urbanization, suggest that infection rates will continue to rise (see, e.g., Guha-Sapir and Schimmer, *Emerging Themes in Epidemiology,* 2: 1-10 (2005)).

The Dengue virus is transmitted to humans by the bite of an *Aedes aegypti* mosquito. Human infections range from asymptomatic to the life-threatening Dengue hemorrhagic fever and Dengue shock syndrome. Dengue fever is an influenza-like disease, frequently resulting in high fever, headache, rash, abdominal pain, and myalgia after an incubation period of four to seven days. In addition to the Dengue fever symptoms, Dengue hemorrhagic fever and Dengue shock syndrome can result in thrombocytopenia, plasma leakage, bleeding, and hypovolemic shock, resulting in shock and eventual death.

Dengue viruses are members of the genus Flavivirus and the family Flaviviridae. The Dengue virus consists of four different serotypes, DV1, DV2, DV3, and DV4. Although infection with one serotype typically confers future protective immunity with respect to that serotype, it does not confer long term immunity to any of the other three serotypes. In addition, prior immunity to one serotype of the Dengue virus may increase the severity of symptoms upon infection of a different serotype of the virus, thus increasing the likelihood that the subject will develop the more severe Dengue hemorrhagic fever or Dengue shock syndrome (see, e.g., Mota and Rico-Hesse, *J. Virol.,* 83(17): 8638-8645 (2009); and Appanna et al., *Clinical and Vaccine Immunology,* 14(8): 969-977 (2007)). There is no specific treatment for Dengue virus. In order to combat Dengue virus infections, the focus has been primarily on mosquito control. However, due to mosquito drug resistance coupled with climate change and the reduction in public health programs, these efforts have been unsuccessful in curtailing the spread of Dengue virus.

Vaccines are the most cost effective and efficient therapeutic interventions for infectious diseases. Research and development directed to a Dengue virus vaccine have not proven successful. Recent efforts have focused primarily on developing vaccines using live attenuated or inactivated virus (see, e.g., U.S. Pat. No. 7,718,359). The current status of Dengue virus vaccine development is reviewed in, for example, Whitehead et al., *Nature Reviews Microbiology,* 5: 518-528 (2007), and Webster et al., *Lancet,* 9(11): 678-687 (2009). DNA-based vaccines such as adenoviral vector vaccines, have been considered (see, e.g., Raviprakash et al., *J. Virol.,* 82(14): 6927-6934 (2008)). However, these vaccines have been unsuccessful due in part to problems with viremia, pre-existing immunity in humans to adenoviral vectors, and concerns associated with an adenoviral vaccine trial associated with HIV (see, e.g., Webster et al., *Lancet,* 9(11): 678-687 (2009)).

Pre-existing immunity results from the generation of antibodies to antigenic epitopes on adenoviral capsid proteins. If sufficient in titer, the antibodies can limit the ability of the vector to be used more than once as an effective gene transfer vehicle. For instance, animal studies demonstrate that intravenous or local administration (e.g., to the lung, heart, or peritoneum) of an adenoviral type 2 or 5 gene transfer vector can result in the production of antibodies directed against the vector which prevent expression from the same serotype vector administered 1 to 2 weeks later (see, e.g., Yei et al., *Hum. Gene Ther.,* 5: 731-744 (1994); Zabner, *Nat. Genet.,* 6: 75-83 (1994); Setoguchi et al., *Am. J. Respir. Cell. Mol. Biol.,* 10: 369-377 (1994); Kass-Eisler et al., *Gene Therapy,* 1: 395-402 (1994); Kass-Eisler et al., *Gene Therapy,* 3: 154-162 (1996)). This is a drawback in adenoviral-mediated gene therapy, since many uses of an adenoviral vector (e.g., for prolonged gene therapy) require repeat administration, inasmuch as the vector does not stably integrate into the host cell genome. The mechanism by which antibodies directed against an adenovirus are able to prevent or reduce expression of an adenoviral-encoded gene is unclear. This phenomenon is loosely referred to as "neutralization," and the responsible antibodies are termed "neutralizing antibodies."

Hexon proteins are the largest and most abundant proteins in the adenovirus capsid, making them a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). However, many of the hexon modifications made to date have not been successful in sufficiently reducing the neutralizing antibody response. These failures are due, at least in part, to the disruption of structural interactions between the loops of the hexon protein, which interferes with the stability of the hexon structure itself, and likely impedes the ability of the hexon region to interact with other capsid proteins. In addition, many of the hexon modification made to date have adversely affected adenovirus growth. Problems associated with virus growth impede the ability to manufacture commercial quantities of adenoviral vectors for, e.g., therapeutic use.

Thus, there remains a need for a composition to effectively deliver Dengue virus antigens to human hosts so as to prevent the onset of disease and/or protect human hosts from further infections. The invention provides such a composition.

BRIEF SUMMARY OF THE INVENTION

The invention provides a replication-deficient adenoviral vector comprising two or more nucleic acid sequences, wherein each nucleic acid sequence encodes a Dengue virus antigen. The adenoviral vector also comprises a chimeric hexon protein. The chimeric hexon protein comprises (a) a first portion comprising at least 10 contiguous amino acid residues of a hexon protein of a wild-type adenovirus of a first serotype, optionally with one amino acid substitution, and (b) a second portion comprising at least one hypervariable region (HVR) of a hexon protein of an adenovirus of a second adenovirus serotype, wherein the first adenovirus serotype is different than the second adenovirus serotype.

The invention also provides a replication-deficient adenoviral vector comprising two or more nucleic acid sequences, wherein each nucleic acid sequence encodes a Dengue virus antigen. The adenoviral vector also comprises a chimeric hexon protein. The chimeric hexon protein comprises (a) a first portion comprising at least 10 contiguous amino acid residues of a hexon protein of a wild-type adenovirus of a first adenovirus serotype, optionally with one amino acid substitution, and (b) a second portion comprising at least one synthetic hypervariable region (HVR) that is not present in the hexon protein of any wild-type adenovirus.

In addition, the invention provides a composition comprising either of the aforesaid replication-deficient adenoviral vectors and a pharmaceutically acceptable carrier.

The invention further provides a composition comprising two replication-deficient adenoviral vectors and a pharmaceutically acceptable carrier. The first adenoviral vector comprises (i) a nucleic acid sequence encoding a serotype DV1 Dengue virus pre-membrane and envelope fusion protein and (ii) a nucleic acid sequence encoding a serotype DV3 Dengue virus pre-membrane and envelope fusion protein. The second adenoviral vector comprises (i) a nucleic acid sequence encoding a serotype DV2 Dengue virus pre-membrane and envelope fusion protein and (ii) a nucleic acid sequence encoding a serotype DV4 Dengue virus pre-membrane and envelope fusion protein.

BRIEF DESCRIPTION OF THE SEVERAL VIEWS OF THE DRAWING

The FIGURE is a graph which depicts experimental data illustrating that the combined administration of two adenoviral vectors that collectively express the DV1, DV2, DV3, and DV4 preM and envelope fusion proteins induce Dengue-specific antibody responses in mice. The y-axis contains the average optical density (OD) values for each Dengue antigen.

DETAILED DESCRIPTION OF THE INVENTION

The invention provides multivalent adenoviral vector-based vaccines directed against Dengue virus. In this respect, the invention provides a replication-deficient adenoviral vector comprising (i) two or more nucleic acid sequences, wherein each nucleic acid sequence encodes a Dengue virus antigen, and (ii) a chimeric hexon protein.

Adenovirus from various origins, subtypes, or mixture of subtypes can be used as the source of the viral genome for the adenoviral vector. Non-human adenovirus (e.g., simian, avian, canine, ovine, or bovine adenoviruses) can be used to generate the adenoviral vector. For example, the adenoviral vector can be based on a simian adenovirus, including both new world and old world monkeys (see, e.g., *Virus Taxonomy: VIIIth Report of the International Committee on Taxonomy of Viruses* (2005)). The phylogeny of adenoviruses that infect primates is disclosed in, e.g., Roy et al., *PLoS Pathog.,* 5(7): e100050. doi:10.1371/journal.ppat.1000503 (2009). For instance, a simian adenovirus can be of serotype 1, 3, 6, 7, 11, 16, 18, 19, 20, 27, 33, 38, 39, 48, 49, or 50, or any other simian adenoviral serotype. Other non-human adenoviruses which can be used in the invention include non-human primate adenoviruses that are genetically and/or phenotypically similar to group C human adenoviruses. A human adenovirus can be used as the source of the viral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 (i.e., Ad1 through Ad51) are available from the American Type Culture Collection (ATCC, Manassas, Va.). Preferably, in the context of the invention, the adenoviral vector is of human subgroup C, especially serotype 2 or even more desirably serotype 5. However, non-group C adenoviruses can be used to prepare adenoviral gene transfer vectors for delivery of gene products to host cells. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Application Publications WO 1997/012986 and WO 1998/053087.

The adenoviral vector can comprise portions of an adenoviral genome of two or more (e.g., a mixture of) subtypes, in addition to containing a nucleic acid sequence encoding the chimeric hexon protein as described herein, and thereby be a "chimeric" adenoviral vector. A chimeric adenoviral vector can comprise an adenoviral genome that is derived from two or more (e.g., 2, 3, 4, etc.) different adenovirus serotypes. In the context of the invention, a chimeric adenoviral vector can comprise approximately different or equal amounts of the genome of each of the two or more different adenovirus serotypes. When the chimeric adenoviral vector genome is comprised of the genomes of two different adenovirus serotypes, the chimeric adenoviral vector genome preferably comprises no more than about 99% (e.g., no more than about 95%, no more than about 85%, no more than about 80%, no more than about 75%, no more than about 60%, no more than about 65%, no more than about 50%, or no more than about 40%) of the genome of one of the adenovirus serotypes, with the remainder of the chimeric adenovirus genome being derived from the genome of the other adenovirus serotype.

The adenoviral vector can be replication-competent, conditionally replication-competent, or replication-deficient.

A replication-competent adenoviral vector can replicate in typical host cells, i.e., cells typically capable of being infected by an adenovirus. A replication-competent adenoviral vector can have one or more mutations as compared to the wild-type adenovirus (e.g., one or more deletions, insertions, and/or substitutions) in the adenoviral genome that do not inhibit viral replication in host cells. For example, the adenoviral vector can have a partial or entire deletion of the adenoviral early region known as the E3 region, which is not essential for propagation of the adenoviral genome.

A conditionally-replicating adenoviral vector is an adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenoviral vector is an adenoviral vector that requires complementation of one or more gene functions or regions of the adenoviral genome that are required for replication, as a result of, for example, a deficiency in one or more replication-essential gene function or regions, such that the adenoviral vector does not replicate in typical host cells, especially those in a human to be infected by the adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Preferably, the adenoviral vector is replication-deficient, such that the replication-deficient adenoviral vector requires complementation of at least one replication-essential gene function of one or more regions of the adenoviral genome for propagation (e.g., to form adenoviral vector particles).

The replication-deficient adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci. USA,* 95: 965-976 (1998); Chen et al., *Proc. Natl. Acad. Sci. USA,* 94: 1645-1650 (1997); and Kochanek et al., *Hum. Gene Ther.,* 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenoviral vector to propagate (e.g., to foam adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenoviral vector to propagate (e.g., to form adenoviral vector particles).

The E3 region does not include any replication-essential gene functions, such that a deletion of the E3 region in part or in whole does not require complementation of any gene functions in the E3 region for the adenoviral vector to propagate (e.g., to form adenoviral vector particles). In the context of the invention, the E3 region is defined as the region that initiates with the open reading frame of the 12.5K protein from the E3 region of human adenovirus 5 (NCBI reference sequence AP_000218) and ends with the open reading frame that encodes the 14.7K protein from the E3 region of human adenovirus 5 (NCBI reference sequence AP_000224.1). The E3 region may be deleted in whole or in part, or retained in whole or in part. The size of the deletion may be tailored so as to retain an adenoviral vector whose genome closely matches the optimum genome packaging size. A larger deletion will accommodate the insertion of larger heterologous nucleic acid sequences in the adenoviral genome.

The E4 region comprises multiple open reading frames (ORFs). An adenoviral vector with a deletion of all of the open reading frames of the E4 region except ORF6, and in some cases ORF3, does not require complementation of any gene functions in the E4 region for the adenoviral vector to propagate (e.g., to form adenoviral vector particles). Conversely, an adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenoviral vector to propagate (e.g., to form adenoviral vector particles). The late regions of the adenoviral genome include the L1, L2, L3, L4, and L5 regions. The adenoviral vector also can have a mutation in the major late promoter (MLP), as discussed in International Patent Application Publication WO 2000/000628, which can render the adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenoviral vector can be deficient in other respects that are not replication-essential. For example, the adenoviral vector can have a partial or entire deletion of the adenoviral early region known as the E3 region, which is not essential for propagation of the adenoviral genome.

In one embodiment, the adenoviral vector is replication-deficient and requires, at most, complementation of the E1 region or the E4 region of the adenoviral genome, for propagation (e.g., to form adenoviral vector particles). Thus, the replication-deficient adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenoviral vector is replication-deficient and requires, at most, complementation of the E2 region, preferably the E2A subregion, of the adenoviral genome, for propagation (e.g., to form adenoviral vector particles). Thus, the replication-deficient adenoviral vector requires complementation of at least one replication-essential gene function of the E2A subregion of the adenoviral genome (denoted an E2A-deficient adenoviral vector) for propagation (e.g., to form adenoviral vector particles). The adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenoviral vector is replication-deficient and requires, at most, complementation of the E1 and E4 regions of the adenoviral genome for propagation (e.g., to form adenoviral vector particles). Thus, the replication-deficient adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenoviral vector preferably requires, at most, complementation of the E1 region of the adenoviral genome for propagation, and does not require complementation of any other deficiency of the adenoviral genome for propagation. More preferably, the adenoviral vector requires, at most, complementation of the E1 and E4 regions of the adenoviral genome for propagation, and does not require complementation of any other deficiency of the adenoviral genome for propagation.

The adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenoviral vector is able to accept inserts of heterologous nucleic acid sequences while retaining the ability to be packaged into adenoviral capsids. A heterologous nucleic acid sequence can be inserted at any position in the adenoviral genome so long as insertion in the position allows for the formation of the adenoviral vector particle. The heterologous nucleic acid sequence preferably is positioned in the E1 region, the E3 region, or the E4 region of the adenoviral genome.

The replication-deficient adenoviral vector of the invention can be produced in complementing cell lines that provide gene functions not present in the replication-deficient adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.,* 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 1995/034671 and Brough et al., *J. Virol.,* 71: 9206-9213 (1997)). Other suitable complementing cell lines to produce the replication-deficient adenoviral vector of the invention include complementing cells that have been generated to propagate adenoviral vectors encoding transgenes whose expression inhibits viral growth in host cells (see, e.g., U.S. Patent Application Publication 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenoviral vector. Alternatively, the inventive adenoviral vector can comprise a non-native replication-essential gene that complements for the one or more replication-essential gene functions lacking in the inventive replication-deficient adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenoviral vector, or an adenovirus of a different species than the inventive adenoviral vector).

The adenoviral vector comprises a chimeric hexon protein. The hexon protein is "chimeric" in that it comprises a sequence of amino acid residues that is not typically found in a hexon protein as isolated from, or identified in, a wild-type adenovirus, which comprises the so-called native hexon protein or "wild-type hexon protein." The chimeric hexon protein thus comprises (or has) a "nonnative amino acid sequence." By "nonnative amino acid sequence" is meant any amino acid sequence (i.e., either component residues or order thereof) that is not found in the native hexon protein of a given serotype of adenovirus, and which preferably is introduced into the hexon protein at the level of gene expression (i.e., by production of a nucleic acid sequence that encodes the nonnative amino acid sequence).

The chimeric adenovirus hexon protein comprises, or alternatively consists of, a first portion related to the wild-type hexon protein of an adenovirus of a first adenovirus serotype and either a second portion related to the wild-type hexon protein of an adenovirus of a second adenovirus serotype that differs from the first adenovirus serotype or a second portion that is a synthetic sequence that is not present in the wild-type hexon protein of the first adenovirus serotype. With the exception of the chimeric hexon protein, the genome of an adenoviral vector as described herein containing the chimeric hexon protein, is based on an adenovirus of the first adenovirus serotype unless otherwise indicated.

In particular, the invention provides a nucleic acid sequence encoding a chimeric adenovirus hexon protein, wherein the chimeric hexon protein comprises, or consists of, (a) a first portion comprising, or consisting of, at least 10 contiguous amino acid residues of hexon protein of a wild-type adenovirus of a first serotype, optionally with one amino acid substitution, and (b) a second portion comprising, or consisting of either (1) at least one hypervariable region (HVR) of a hexon protein of an adenovirus of a second adenovirus serotype, wherein the first adenovirus serotype is different than the second adenovirus serotype, or (2) at least one synthetic hypervariable region (HVR) that is not present in the hexon protein of any wild-type adenovirus.

The chimeric hexon protein desirably is generated by replacing one or more portions of an amino acid sequence of a wild-type hexon protein of an adenovirus of a first serotype (e.g., a serotype 5 adenovirus) with either (1) one or more portions of an amino acid sequence of a wild-type hexon protein of an adenovirus of a second, and different, serotype (e.g., an adenovirus of a serotype other than serotype 5) or (2) one or more synthetic amino acid sequences that are not present in the wild-type hexon protein of the adenovirus of the first serotype (e.g., a serotype 5 adenovirus). The aforementioned replacement in the wild-type hexon protein of the adenovirus of the first serotype desirably is effected by making the appropriate changes in the wild-type nucleic acid sequence encoding the hexon protein of the adenovirus of the first serotype, such that the modified nucleic acid sequence encodes the chimeric hexon protein described herein.

The terms "nucleic acid sequence," "nucleic acid," "nucleic acid molecule," and "polynucleotide" encompass a polymer of DNA or RNA, i.e., a polynucleotide, which can be single-stranded or double-stranded and which can contain non-natural or altered nucleotides. In this respect, these terms include, as equivalents, analogs of either RNA or DNA made from nucleotide analogs and modified polynucleotides such as, though not limited to, methylated and/or capped polynucleotides.

By "portion" is meant an amino acid sequence that comprises at least three amino acids (e.g., about 3 to about 800 amino acids). Preferably, a "portion" comprises 10 or more (e.g., 10 or more, 15 or more, 20 or more, 25 or more, 30 or more, 40 or more, 50 or more, or 100 or more) amino acid residues, but less than the entire wild-type hexon protein (e.g., 800 or less, 700 or less, 600 or less, 500 or less, 400 or less, 300 or less, 200 or less, or 100 or less amino acid residues). For example, a portion can be about 10 to about 500 amino acids (e.g., about 10, 100, 300, or 500 amino acids), about 10 to about 300 amino acids (e.g., about 20, 50, or 200 amino acids), or about 10 to about 100 amino acids (e.g., about 15, 40, 60, 70, or 90 amino acids), or a range defined by any two of the foregoing values. More preferably, a "portion" comprises no more than about 300 amino acids (e.g., about 10 to about 250 amino acids, about 10 to about 200 amino acids, or about 50 to about 100 amino acids, or a range defined by any two of the foregoing values).

The first portion of the chimeric hexon protein comprises at least 10 contiguous amino acid residues of a hexon protein of a wild-type adenovirus of a first adenovirus serotype, optionally with one amino acid substitution. The first adenovirus serotype from which the first portion of the chimeric hexon protein is derived or obtained from can be any adenovirus serotype described herein, but preferably the first adenovirus serotype is serotype 5. The first adenovirus serotype can be a human or non-human adenovirus serotype. In a preferred embodiment, the first adenovirus serotype is human serotype 5.

When the first portion of the chimeric hexon protein comprises at least 10 contiguous amino acid residues of the hexon protein of the wild-type serotype 5 adenovirus with one amino acid substitution, the first portion include a point mutation, i.e., a single amino acid residue replacement, as compared to the corresponding portion of the hexon protein of the wild-type serotype 5 adenovirus. The point mutation can be effected in any suitable manner. Desirably, the nucleic acid sequence which encodes the first portion of the chimeric hexon protein comprises a mutation, e.g., a replacement of one or more nucleotides, that results in a single amino acid substitution in the protein encoded thereby. The nucleic acid sequence can be mutated by any suitable method known in the art, such as, for example, by insertion, deletion, and/or substitution. For example, mutations may be introduced into a nucleic acid sequence randomly or in a site-specific manner. Random mutations may be generated, for example, by error-prone PCR of a template sequence. A preferred means for introducing random mutations in is the Genemorph II Random Mutagenesis Kit (Stratagene, La Jolla, Calif.). Site-specific mutations can be introduced, for example, by ligating into an expression vector a synthesized oligonucleotide comprising the modified site. Alternately, oligonucleotide-directed site-specific mutagenesis procedures can be used, such as those disclosed in Walder et al., *Gene,* 42: 133 (1986); Bauer et al., *Gene,* 37: 73 (1985); Craik, *Biotechniques,* 12-19

(January 1995); and U.S. Pat. Nos. 4,518,584 and 4,737,462. A preferred means for introducing site-specific mutations is the QuikChange Site-Directed Mutagenesis Kit (Stratagene, La Jolla, Calif.).

The amino acid substitution can be of any amino acid residue with any other amino acid residue. As such, the amino acid substitution can be a conservative amino acid substitution or mutation, a semi-conservative substitution or mutation, or a non-conservative substitution or mutation. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, *Principles of Protein Structure,* Springer-Verlag, New York (1979)). According to such analyses, groups of amino acids may be defined where amino acids within a group exchange preferentially with each other, and therefore resemble each other most in their impact on the overall protein structure (Schulz, G. E. and R. H. Schirmer, supra). Examples of conservative mutations include amino acid substitutions of amino acids within the sub-groups described below, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —$NH_2$ can be maintained. "Semi-conservative substitutions" or "semi-conservative mutations" include amino acid substitutions of amino acids with the same groups listed below, but that do not share the same sub-group. For example, the mutation of aspartic acid for asparagine, or asparagine for lysine, each involves amino acids within the same group, but different sub-groups. "Non-conservative substitutions" or "non-conservative mutations" involve amino acid substitutions between different groups, for example lysine for tryptophan, or phenylalanine for serine.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aromatic amino acids may be sub-divided into two sub-groups: the "nitrogen ring sub-group" consisting of histidine and tryptophan, and the "phenyl sub-group" consisting of phenylalanine and tyrosine.

Aliphatic amino acids may be sub-divided into four sub-groups. The "large aliphatic non-polar sub-group" consists of valine, leucine and isoleucine, the "aliphatic slightly-polar sub-group" consists of methionine, serine, threonine, and cysteine, the "aliphatic polar/charged sub-group" consists of glutamic acid, aspartic acid, asparagine, glutamine, lysine, and arginine, and the "small-residue sub-group" consists of glycine and alanine. The group of charged/polar amino acids may be sub-divided into three sub-groups: the "positively-charged sub-group," consisting of lysine and arginine, the "negatively-charged sub-group," consisting of glutamic acid and aspartic acid, and the "polar sub-group" consisting of asparagine and glutamine.

The point mutation described herein can result in an amino acid substitution at any suitable residue. Preferably, the amino acid substitution is at residue 342 of the hexon protein of the wild-type serotype 5 adenovirus. The numbering of amino acid positions in the chimeric hexon protein used herein is based on the hexon amino acid sequence including the initial methionine residue. The point mutation described herein also can result in a conservative, semi-conservative, or non-conservative amino acid substitution as described herein. Preferably, the amino acid substitution is a threonine (T) to methionine (M) substitution.

The second portion of the chimeric hexon protein comprises at least one HVR that is not present in the hexon protein of the wild-type adenovirus of the first adenovirus serotype.

In a first embodiment of the second portion, the second portion of the chimeric hexon protein comprises at least one HVR of a hexon protein of an adenovirus of a second adenovirus serotype, wherein the second adenovirus serotype is not the same as the first adenovirus serotype (i.e., wherein the first and second serotypes are different). Thus, when the first adenovirus serotype is serotype 5, the second adenovirus serotype is not serotype 5. The second portion of the chimeric hexon protein desirably comprises at least one HVR that occurs naturally in a hexon protein of a wild-type adenovirus (i.e., a wild-type hexon protein) of a second serotype that differs from the first serotype (e.g., a second serotype that is not serotype 5).

The one or more HVRs of the wild-type hexon protein of the second adenovirus serotype desirably replace one or more HVRs of the wild-type hexon protein of the first adenovirus serotype in providing the chimeric hexon protein. The HVRs of the hexon protein are located in the loops of the hexon protein (DE1 and FG1), which are found at the top of the hexon molecule (see, e.g., Rux et al., *J. Virol.,* 77(17): 9553-9566 (2003)). The hypervariable regions vary in length and sequence between adenoviral serotypes (Crawford-Miksza et al., *J. Virol.,* 70: 1836-1844 (1996)). The HVR regions include the HVR1 region, the HVR2 region, the HVR3 region, the HVR4 region, the HVR5 region, the HVR6 region, the HVR7 region, the HVR8 region, and the HVR9 region.

The amino acid sequence of a wild-type serotype 5 hexon protein comprises SEQ ID NO: 1. Preferably, amino acid residues within the FG1, FG2, or DE1 loops of a hexon protein of a serotype 5 adenovirus are deleted and replaced with corresponding amino acid residues from a hexon protein of a second, and different, adenovirus serotype (i.e., corresponding amino acid residues from a hexon protein of a wild-type adenovirus of a serotype other than serotype 5). An entire loop region can be removed from a hexon protein of a wild-type serotype 5 adenovirus and replaced with the corresponding loop region of a hexon protein of a wild-type adenovirus of a serotype other than serotype 5. Alternatively, one or more portions of a loop region can be removed from the hexon protein of a wild-type serotype 5 adenovirus and replaced with one or more corresponding portions of a loop region of a hexon protein of a wild-type adenovirus of a serotype other than serotype 5. Similarly, one or more hexon loops, or portions thereof, of a hexon protein of a wild-type serotype 5 adenovirus can be removed and replaced with the corresponding amino acid sequences of a hexon protein of a wild-type adenovirus of a serotype other than serotype 5. Preferably, the second adenovirus serotype is serotype 43, 48, or 34. Thus, in one embodiment, one or more hexon loops, or portions thereof, of a hexon protein of a wild-type serotype 5 adenovirus are removed and replaced with corresponding amino acid sequences of a hexon protein of a wild-type adenovirus of serotype 43, 48, or 34. For example, the chimeric hexon protein can have the amino acid sequence of SEQ ID NO: 2, SEQ ID NO: 3, SEQ ID NO: 4, SEQ ID NO: 5, or SEQ ID NO: 6. In a preferred embodiment, all nine HVRs of a hexon protein of a wild-type serotype 5 adenovirus are removed and replaced with the corresponding amino acid sequences of a hexon protein of a wild-type adenovirus of serotype 43. The structure of serotype 5 hexon proteins and methods of modifying hexon proteins are disclosed in, for example, Rux et al., *J. Virol.,* 77(17): 9553-9566 (2003), and U.S. Pat. No. 6,127,525.

The second portion of the chimeric hexon protein can comprise any HVR of the wild-type adenovirus of the second serotype, as well as any number of HVRs of the wild-type adenovirus of the second adenovirus serotype. For example, the second portion of the chimeric hexon protein can comprise one or more of HVR1, HVR2, HVR3, HVR4, HVR5, HVR6, HVR7, HVR8, and HVR9 of a hexon protein of a wild-type adenovirus of the second serotype. The second portion of the chimeric hexon protein preferably comprises at least one HVR of the DE1 loop and/or FG1 loop of a wild-type hexon protein of the second adenovirus serotype (e.g., 1, 2, 3, 4, 5, 6, 7, 8, or 9 HVRs). More preferably, the second portion of the chimeric hexon protein comprises three or more HVRs of the DE1 loop and/or FG1 loop of a wild-type hexon protein of the second adenovirus serotype (e.g., 3, 4, 5, 6, 7, 8, or 9 HVRs). In a particularly preferred embodiment, the second portion of the chimeric hexon protein comprises six HVRs of the DE1 loop of a wild-type hexon protein of the second adenovirus serotype and/or three HVRs of the FG1 loop of a wild-type hexon protein of the second adenovirus serotype. Thus, for example, a region of a wild-type hexon protein of adenovirus serotype 5 (Ad5) comprising HVR1-HVR6 can be deleted and replaced with a region comprising HVR1-HVR6 of a hexon protein of a wild-type adenovirus of serotype 43 (Ad43). In another example, a region of a wild-type hexon protein of adenovirus serotype 5 (Ad5) comprising HVR1-HVR9 can be deleted and replaced with a region of a wild-type hexon protein of adenovirus serotype 48 (Ad48) comprising HVR1-HVR9.

As is apparent from the foregoing description, the second portion of the chimeric hexon protein can comprise any portion of the hexon protein, in addition to the at least one HVR, of the wild-type adenovirus of the second serotype. For example, the second portion of the chimeric hexon protein can comprise the entirety of the DE1 and/or FG1 loops of a hexon protein of a wild-type adenovirus of a second serotype.

The second portion of the chimeric hexon protein optionally further comprises at least one HVR that is synthetically-generated (i.e., a "synthetic HVR"). By "synthetic HVR" is meant that the HVR does not occur naturally in a wild-type hexon protein of an adenovirus of any serotype and preferably is generated using routine biochemical techniques. In this respect, a synthetic HVR can be a native adenovirus HVR that has been modified in any suitable manner, e.g., by deletion, insertion, or substitution of one or more amino acid residues, using routine molecular biology methods known in the art. Preferably, however, a synthetic HVR is not derived from an adenovirus. In this respect, the HVR can be a synthetically-generated random amino acid sequence that comprises about 1 to about 40 amino acid residues (e.g., about 1, 5, 10, 15, 20, 25, 30, 35, or 40 amino acid residues, or a range defined by any two of the foregoing values). A preferred random amino acid sequence is one that has been selected from among several other random amino acid sequences because the random amino acid sequence does not impede, and preferably enhances, growth of an adenoviral vector and/or because the random amino acid sequence reduces host immune responses directed against the chimeric hexon protein. Thus, a random amino acid sequence also can be referred to as a "selected random amino acid sequence."

In a preferred embodiment, the second portion of the chimeric hexon protein comprises two or more HVRs, with at least one HVR being a synthetic HVR, especially wherein a random amino acid sequence desirably is utilized as at least one synthetic HVR. In other words, in such a preferred embodiment, the second portion of the chimeric hexon protein comprises one or more wild-type HVRs of the second adenovirus serotype and one or more synthetic HVRs, wherein at least one synthetic HVR desirably is a synthetically-derived random amino acid sequence as described herein.

The synthetic HVR can be an epitope of a Dengue virus antigen. An "antigen" is a molecule that induces an immune response in a mammal. An "immune response" can entail, for example, antibody production and/or the activation of immune effector cells (e.g., T cells). An antigen in the context of the invention can comprise any subunit, fragment, or epitope of any proteinaceous molecule, including a protein or peptide of Dengue virus, which ideally provokes an immune response in mammal, preferably leading to protective immunity. By "epitope" is meant a sequence on an antigen that is recognized by an antibody or an antigen receptor. Epitopes also are referred to in the art as "antigenic determinants."

Desirably, the second portion of the chimeric hexon protein comprises an epitope of a Dengue virus antigen in place of one wild-type HVR of the second adenovirus serotype. In other words, the second portion of the chimeric hexon protein desirably comprises one or more wild-type HVRs of the second adenovirus serotype and one or more synthetic HVRs, wherein at least one synthetic HVR is an epitope of a Dengue virus antigen as described herein (e.g., desirably an epitope of a Dengue virus envelope protein). Preferably, the second portion of the chimeric hexon protein comprises at least one wild-type HVR of the second adenovirus serotype and at least two synthetic HVRs, wherein each of the at least two synthetic HVRs is an epitope of a Dengue virus antigen. In this embodiment, the same epitope can be utilized as each synthetic HVR, or different epitopes of a Dengue virus antigen can be used as the synthetic HVRs. For example, the second portion of the chimeric hexon protein can comprise six HVRs of the DE1 loop of a wild-type hexon protein of the second adenovirus serotype, except that HVR1, HVR5, or both HVR1 and HVR5 are replaced with an epitope of a Dengue virus antigen. Epitope amino acid sequences can be inserted into the second portion of the chimeric hexon protein by effecting the removal of amino acid residues within one or more of the hypervariable regions of the second portion and addition of the epitope amino acid sequence (i.e., replacement of the removed amino acid residues with the epitope amino acid sequence) using methods described herein.

In a second embodiment of the second portion, the second portion of the chimeric hexon protein comprises at least one synthetic HVR that is not present in the hexon protein of any wild-type adenovirus. Preferably, the second portion of the chimeric hexon protein comprises two or more synthetic HVRs (e.g., 3 or more, 4 or more, 5 or more, 6 or more, 7 or more, 8 or more, or 9 synthetic HVRs, or a range defined by any two of the foregoing values) that are not present in the hexon protein of any wild-type adenovirus. More preferably, the second portion of the chimeric hexon protein comprises three synthetic HVRs that are not present in the hexon protein of any wild-type adenovirus. Most preferably, the second portion of the chimeric hexon protein comprises nine synthetic HVRs that are not present in the hexon protein of any wild-type adenovirus. The synthetic HVR can be any suitable synthetic HVR described herein, such a random amino acid sequence or an epitope of a Dengue virus antigen.

The one or more synthetic HVRs desirably replace one or more HVRs of the wild-type hexon protein of the first adenovirus serotype in providing the chimeric hexon protein. As described above, the HVRs of the hexon protein are located in the loops of the hexon protein (DE1 and FG1), which are found at the top of the hexon molecule (see, e.g., Rux et al., *J. Virol.,* 77(17): 9553-9566 (2003)). The hypervariable regions vary in length and sequence between adenoviral serotypes (Crawford-Miksza et al., *J. Virol.,* 70: 1836-1844 (1996)). The HVR regions include the HVR1 region, the HVR2 region, the HVR3 region, the HVR4 region, the HVR5 region, the HVR6 region, the HVR7 region, the HVR8 region, and the HVR9 region. Thus, for example, a region of a wild-type hexon protein of adenovirus serotype 5 (Ad5) comprising HVR1-HVR6 can be deleted and replaced with synthetic HVRs as described herein. In another example, a region of a wild-type hexon protein of adenovirus serotype 5 (Ad5) comprising HVR1-HVR9 can be deleted and replaced synthetic HVRs as described herein.

It will be appreciated that incorporating a Dengue virus epitope into the adenovirus capsid can enhance the immune response elicited by the inventive adenoviral vector. The epitope can be from any Dengue virus antigen described herein. Preferably, the epitope is obtained or derived from a Dengue virus envelope protein. Suitable Dengue virus antigens include all or part of Dengue protein M, Dengue protein E, Dengue D1NS1, Dengue D1NS2, and Dengue D1NS3.

The chimeric adenovirus hexon protein has a decreased ability or an inability to be recognized by an antibody (e.g., a neutralizing antibody) directed against a corresponding wild-type hexon protein of an adenovirus. A "neutralizing antibody" is an antibody that is purified from, or is present in, serum. As used herein, an antibody can be a single antibody or a plurality of antibodies. An antibody is "neutralizing" if the antibody inhibits infectivity of (i.e., cell entry by), or gene expression commanded by, an adenovirus comprising a wild-type hexon protein, or if the antibody exerts a substantial deleterious effect on infectivity of, or gene expression commanded by, an adenovirus comprising a wild-type hexon protein. In one embodiment, the removal of one or more epitopes for a neutralizing antibody present in a wild-type hexon protein of an adenovirus to generate a chimeric adenovirus hexon protein will result in a decreased ability or inability of the chimeric hexon protein to be recognized by the neutralizing antibody.

An ability or inability of a chimeric hexon protein to "be recognized by" (i.e., interact with) a neutralizing antibody directed against a wild-type hexon protein of an adenovirus can be assessed by a variety of means known to those skilled in the art. For example, a decreased ability or inability to interact with a neutralizing antibody directed against wild-type hexon protein can be demonstrated by means of a neutralization test (see, e.g., Crawford-Miksza et al., supra; Mastrangeli et al., *Human Gene Therapy,* 7: 79-87 (1996)), or as further described herein.

Generally, an "inability" of a chimeric adenovirus hexon protein to be recognized by a neutralizing antibody directed against a wild-type hexon protein of an adenovirus means that such an antibody does not interact with the chimeric hexon protein and/or exhibits no substantial deleterious effect on infectivity of, or gene expression commanded by, an adenovirus comprising the chimeric hexon protein.

A "decreased ability" to be recognized by a neutralizing antibody directed against a wild-type hexon protein of an adenovirus refers to any decrease in the ability of the chimeric adenovirus hexon protein to be recognized by an antibody directed against a wild-type hexon protein of an adenovirus of the first adenovirus serotype, as described herein. When such ability/inability is assessed by means of a neutralization test in particular, preferably a "decreased ability" to be recognized by a neutralizing antibody directed against a wild-type hexon protein of an adenovirus of the first adenovirus serotype reflects about a 10% to about a 99% increase in the ability of an adenoviral vector comprising the chimeric hexon protein to cause a visible cytopathic effect (c.p.e.) in cells such as A549 cells or COS-1 cells (or other such cells appropriate for a neutralization assay) in the presence of the neutralizing antibody as compared to an adenoviral vector comprising the wild-type hexon protein of the first adenovirus serotype against which the neutralizing antibody is directed.

A decreased ability or inability of an adenovirus chimeric hexon protein to interact with a neutralizing antibody can be shown by, for example, a reduction of inhibition (from about 10% to about 99%) or no inhibition at all of cell infectivity by a recombinant adenoviral vector containing the chimeric hexon protein as compared to a recombinant adenoviral vector containing a wild-type hexon protein of the first adenovirus serotype (e.g., serotype 5).

An adenoviral vector that comprises the chimeric hexon protein described herein desirably exhibits a growth rate in cells that is similar to the growth rate of an adenoviral vector comprising a wild-type hexon protein of an adenovirus of the first adenovirus serotype. In this respect, an adenoviral vector comprising the chimeric adenovirus hexon protein preferably exhibits no more than a three-fold decrease in growth in cells as compared to that of an adenoviral vector comprising a wild-type adenovirus hexon protein of an adenovirus of the first adenovirus serotype. More preferably, an adenoviral vector comprising the chimeric adenovirus hexon protein exhibits no more than about a 2-fold decrease in growth in cells or no more than about a 1.5-fold decrease in growth in cells as compared to that of an adenoviral vector comprising a wild-type hexon protein of an adenovirus of the first adenovirus serotype. For example, an adenoviral vector comprising the chimeric adenovirus hexon protein desirably exhibits no more than about a 1.4-fold decrease in growth, no more than about a 1.3-fold decrease in growth, no more than about a 1.2-fold decrease in growth, or no more than about a 1.1-fold decrease in growth in cells as compared to that of an adenoviral vector comprising a wild-type hexon protein of an adenovirus of the first adenovirus serotype. The vectors can be grown in any suitable cells, such as HEK 293 cells.

In addition to the hexon protein, other coat proteins of an adenoviral vector can be manipulated to alter the binding specificity or recognition of the virus for a viral receptor on a potential host cell. Such manipulations can include deletion of regions of the fiber or penton, insertions of various native or non-native ligands into portions of the coat proteins, and the like. Manipulation of coat proteins can broaden the range of cells infected by the adenoviral vector or enable targeting of the adenoviral vector to a specific cell type.

The adenoviral vector can comprise a modified fiber protein. The fiber protein is "modified" in that it comprises a nonnative amino acid sequence, in addition to or in place of a wild-type fiber amino acid sequence of an adenovirus of the first adenovirus serotype. Any suitable amino acid residue(s) of a wild-type fiber protein of the first adenovirus serotype that mediates or assists in the interaction between the fiber knob and the native cellular receptor can be modified or removed, so long as the fiber protein is able to trimerize. Similarly, amino acids can be added to the fiber knob as long as the fiber protein retains the ability to trimerize.

At least a portion of the wild-type fiber protein of an adenovirus of the first serotype optionally can be removed and replaced with a corresponding portion of a wild-type fiber protein from a third adenovirus serotype. The third adenovirus serotype preferably is different than the first adenovirus serotype. Preferably, the entire wild-type fiber protein of an adenovirus of the first adenovirus serotype is replaced with a fiber protein from an adenovirus of a third serotype. While the third adenovirus serotype is different than the first adenovirus serotype, the third adenovirus serotype can be the same as the second adenovirus serotype from which the second portion of the chimeric hexon protein is derived. Alternatively, the third adenovirus serotype can be different than the second adenovirus serotype from which the second portion of the chimeric hexon protein is derived. The third adenovirus serotype can be any human or non-human (e.g., simian) adenovirus serotype described herein.

The modified fiber protein can comprise a non-native amino acid sequence that confers to the modified fiber protein the ability to bind to an immune cell more efficiently than a wild-type fiber protein from an adenovirus of the first serotype. In particular, the adenoviral vector can comprise a modified adenoviral fiber protein comprising a non-native amino acid sequence which facilitates uptake of the adenoviral vector by immune cells, preferably antigen presenting cells, such as dendritic cells, monocytes, and macrophages. The adenoviral vector can comprise a modified fiber protein comprising an amino acid sequence (e.g., a non-native amino acid sequence) comprising an RGD motif, which increases transduction efficiency of the adenoviral vector into dendritic cells. The RGD-motif, or any non-native amino acid sequence, preferably is inserted into the adenoviral fiber knob region, ideally in an exposed loop of the adenoviral knob, such as the HI loop. A non-native amino acid sequence also can be appended to the C-terminus of the adenoviral fiber protein, optionally via a spacer sequence.

Modifications to adenovirus coat proteins, including methods for generating chimeric fiber proteins, are described in, for example, e.g., U.S. Pat. Nos. 5,543,328; 5,559,099; 5,712,136; 5,731,190; 5,756,086; 5,770,442; 5,846,782; 5,871,727; 5,885,808; 5,922,315; 5,962,311; 5,965,541; 6,057,155; 6,127,525; 6,153,435; 6,329,190; 6,455,314; 6,465,253; 6,576,456; 6,649,407; and 6,740,525; U.S. Patent Application Publications 2001/0047081 A1, 2002/0099024 A1, 2002/0151027 A1, 2003/0022355 A1, and 2003/0099619 A1, and International Patent Application Publications WO 1996/007734, WO 1996/026281, WO 1997/020051, WO 1998/007865, WO 1998/007877, WO 1998/040509, WO 1998/054346, WO 2000/015823, WO 2001/058940, and WO 2001/092549.

The adenoviral vector comprises at least two nucleic acid sequences, each of which encodes an antigen. Any type of nucleic acid sequence (e.g., DNA, RNA, and cDNA) that can be inserted into an adenoviral vector can be used in connection with the invention. Preferably, each nucleic acid sequence is DNA and encodes a protein (i.e., two or more nucleic acid sequences encoding two or more proteins).

Each nucleic acid sequence encodes a Dengue virus antigen. A Dengue virus antigen in the context of the invention can comprise any proteinaceous Dengue virus molecule or portion thereof that provokes an immune response in a mammal. A "Dengue virus molecule" is a molecule that is a part of a Dengue virus, is encoded by a nucleic acid sequence of a Dengue virus, or is derived from or synthetically based upon any such molecule. Administration of an Dengue virus antigen that provokes an immune response in accordance with the invention preferably leads to protective immunity against one or more Dengue virus serotypes. In this regard, an "immune response" to Dengue virus is an immune response to any one or more Dengue virus antigens.

Dengue viruses are classified as belonging to one of four different serotypes, i.e., DV1, DV2, DV3, and DV4. These four serotypes have about 60-80% homology between each other. The genomes of a number of Dengue virus serotypes have been sequenced. For example, the complete genome of a DV3 Dengue virus has been sequenced and is disclosed in Osatomi et al., *Virology,* 176(2): 643-7 (1990), and the complete genome sequence of DV2 Dengue virus is disclosed in Tolou et al., *Biochemical and Biophysical Research Comm.,* 277(1): 89-92 (2000). Thus, one of ordinary skill in the art can identify and isolate an appropriate Dengue virus antigen using routine methods known in the art.

The Dengue virus genome is a positive-sense single stranded RNA molecule of about 11 kb in length. It includes seven non-structural proteins (NS 1-7) and three structural proteins, including a capsid (C), pre-membrane/membrane (PreM/M), and envelope (E) (see, e.g., Crill et al., *PLoS One,* 4(4): 1-17 (2009)). Dengue virions contain a lipid bilayer covered with pre-membrane/membrane proteins and envelope proteins which form dimers on its surface. The pre-membrane protein aids in the folding of the envelope protein and is cleaved during late stage virion assembly, resulting in a rearrangement of the membrane and envelope proteins on the surface of mature virions. The envelope protein facilitates cell attachment and is the primary target of protective antibodies. Dengue virus envelope proteins contain three structural domains, a central domain, a highly conserved dimerization domain, and a receptor-binding domain, all of which are essential for viral infectivity (see, e.g., Whitehead et al., *Nature Reviews Microbiology,* 5: 518-528 (2007)).

In the context of the invention, the adenoviral vector comprises two or more nucleic acid sequences, each of which encodes any Dengue virus antigen. Preferably, the Dengue virus antigen includes all or part of, for example, a pre-membrane protein, an envelope protein, or chimeric or fusion proteins comprising portions thereof. In a preferred embodiment of the invention, the nucleic acid sequences encoding Dengue virus antigens comprise codons expressed more frequently in humans than in Dengue virus. While the genetic code is generally universal across species, the choice among synonymous codons is often species-dependent. One of ordinary skill in the art would appreciate that, to achieve maximum protection against Dengue virus infection, the adenoviral vector must be capable of expressing high levels of Dengue virus antigens in a mammalian, preferably a human, host. In this respect, the nucleic acid sequence preferably encodes the native amino acid sequence of an Dengue virus antigen, but comprises codons that are expressed more frequently in mammals (e.g., humans) than in Dengue virus. Changing all native Dengue virus codons to the most frequently used in mammals will increase expression of the Dengue virus antigen in a mammal (e.g., a human). Such modified nucleic acid sequences are commonly described in the art as "humanized," as "codon-optimized," or as utilizing "mammalian-preferred" or "human-preferred" codons. In the context of the invention, codon optimization eliminates stretches of homologous sequences in the at least two Dengue virus antigen-encoding nucleic acid sequences that are present in a single adenoviral vector and maintains optimal codons for expression in humans.

In the context of the invention, a Dengue virus nucleic acid sequence is said to be "codon-optimized" if at least about 60% (e.g., at least about 70%, at least about 80%, or at least about 90%) of the wild-type codons in the nucleic acid sequence are modified to encode mammalian-preferred codons. That is, a Dengue virus nucleic acid sequence is codon-optimized if at least about 60% of the codons encoded therein are mammalian-preferred codons. Preferred codon-optimized nucleic acid sequences encoding a Dengue virus PreM and envelope fusion protein comprise, for example, SEQ ID NO: 7, SEQ ID NO: 8, SEQ ID NO: 9, or SEQ ID NO: 10. However, the invention is not limited to these exemplary sequences. Indeed, genetic sequences can vary between different strains, and this natural scope of allelic variation is included within the scope of the invention. Additionally and alternatively, the codon-optimized nucleic acid sequence encoding a Dengue virus antigen can be any sequence that hybridizes to an above-described sequences under at least moderate, preferably high, stringency conditions, such as those described in, e.g., Sambrook et al., *Molecular Cloning, a Laboratory Manual, 3rd edition*, Cold Spring Harbor Press, Cold Spring Harbor, N.Y. (2001). Determining the degree of homology can be accomplished using any suitable method (e.g., BLASTnr, provided by GenBank).

The adenoviral vector can comprise more than two nucleic acid sequences, each of which encodes a Dengue virus antigen. Thus, the invention provides an adenoviral vector comprising two or more (e.g., 2, 3, 4, 5, 6, 7, 8, 9, 10, or more) nucleic acid sequences, each of which encodes a Dengue virus antigen. When the adenoviral vector comprises multiple (i.e., two or more) Dengue virus antigen-encoding nucleic acid sequences, each nucleic acid sequence can encode the same Dengue virus antigen. Alternatively, the adenoviral vector can comprise multiple nucleic acid sequences encoding two or more different Dengue virus antigens.

In addition, each of the two or more nucleic acid sequences preferably encodes a Dengue virus antigen from a different Dengue virus serotype. For example, the adenoviral vector can comprise two nucleic acid sequences, wherein the first nucleic acid sequence encodes a Dengue virus antigen derived from the DV1 serotype, and the second nucleic acid sequence encodes a Dengue virus antigen derived from the DV2, DV3, or DV4 serotype. Also, for example, the adenoviral vector can comprise two nucleic acid sequences, wherein the first nucleic acid sequence encodes a Dengue virus antigen derived from the DV2 serotype, and the second nucleic acid sequence encodes a Dengue virus antigen derived from the DV1, DV3, or DV4 serotype. In a further example, the adenoviral vector can comprise two nucleic acid sequences, wherein the first nucleic acid sequence encodes a Dengue virus antigen derived from the DV3 serotype, and the second nucleic acid sequence encodes a Dengue virus antigen derived from the DV1, DV2, or DV4 serotype. In yet another example, the adenoviral vector can comprise two nucleic acid sequences, wherein the first nucleic acid sequence encodes a Dengue virus antigen derived from the DV4 serotype, and the second nucleic acid sequence encodes a Dengue virus antigen derived from the DV1, DV2, or DV3 serotype.

Each of the nucleic acid sequences encoding a Dengue virus antigen preferably is located in the E1 region or the E4 region of the adenoviral genome. Thus, in accordance with the invention, at least one Dengue virus antigen-encoding nucleic acid sequence (e.g., one, two, three, or more Dengue virus antigen-encoding nucleic acid sequences) is located in the E1 region of the adenoviral genome, and at least one Dengue virus antigen-encoding nucleic acid sequence (e.g., one, two, three, or more Dengue virus antigen-encoding nucleic acid sequences) can be located in the E4 region of the adenoviral genome. In embodiments where the adenoviral vector comprises three or more nucleic acid sequences, at least one Dengue virus antigen-encoding nucleic acid sequence preferably is located in the E1 region of the adenoviral genome, and at least two Dengue virus antigen-encoding nucleic acid sequences preferably are located in the E4 region of the adenoviral genome. Alternatively, at least two Dengue virus antigen-encoding nucleic acid sequences can be located in the E1 region of the adenoviral genome, and at least one Dengue virus antigen-encoding nucleic acid sequence can be located in the E4 region of the adenoviral genome. While not preferred, all of the Dengue virus antigen-encoding nucleic acid sequences can be located in either the E1 region or the E4 region of the adenoviral genome. The insertion of a nucleic acid sequence into the adenoviral genome (e.g., into the E1 region of the genome) can be facilitated by known methods, for example, by the introduction of a unique restriction site at a given position of the adenoviral genome. As set forth above, preferably all or part of the E3 region of the adenoviral vector also is deleted.

Each of the nucleic acid sequences encoding a Dengue virus antigen can be inserted into the adenoviral genome in a 3'-5' orientation, e.g., oriented such that the direction of transcription of the nucleic acid sequence is opposite that of the surrounding adjacent adenoviral genome. However, it is also appropriate for a nucleic acid sequence encoding a Dengue virus antigen to be inserted in a 5'-3' orientation with respect to the direction of transcription of the surrounding genome. In this regard, it is possible for the inventive adenoviral vector to comprise at least one Dengue virus antigen-encoding nucleic acid sequence inserted into, for example, the E1 region in a 5'-3' orientation, and at least one Dengue virus antigen-encoding nucleic acid sequence inserted into the E4 region in a 5'-3' orientation. Alternatively, the inventive adenoviral vector can comprise at least one Dengue virus antigen-encoding nucleic acid sequence inserted into the E1 region in a 5'-3' orientation, and at least one Dengue virus antigen-encoding nucleic acid sequence inserted into the E4 region in a 3'-5' orientation. In yet another embodiment, the inventive adenoviral vector can comprise at least one Dengue virus antigen-encoding nucleic acid sequence inserted into the E1 region in a 3'-5' orientation, and at least one Dengue virus antigen-encoding nucleic acid sequence inserted into the E4 region in a 5'-3' orientation with respect to the direction of transcription of the surrounding genome.

In addition to the two or more nucleic acid sequences encoding Dengue virus antigens, the adenoviral vector preferably comprises expression control sequences, such as promoters, enhancers, polyadenylation signals, protease cleavage sites, transcription terminators, internal ribosome entry sites (IRES), and the like, that provide for the expression of the nucleic acid sequences in a host cell. Exemplary expression control sequences are known in the art and are described in, for example, Goeddel, *Gene Expression Technology: Methods in Enzymology*, Vol. 185, Academic Press, San Diego, Calif. (1990). Ideally, each of the Dengue virus antigen-encoding nucleic acid sequences is operably linked to a promoter and a polyadenylation sequence. A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter (human or mouse), and the SV40 promoter. Preferably, the promoter is a human CMV (hCMV) promoter or a mouse CMV (mCMV) promoter. Inducible promoters include, for example, the Tet system (U.S. Pat. Nos. 5,464,758 and 5,814,618), the Ecdysone inducible system (see, e.g., No et al., *Proc. Natl. Acad. Sci.,* 93: 3346-3351 (1996)), the T-REx™ system (Invitrogen, Carlsbad, Calif.), LACSWITCH™ System (Stratagene, San Diego, Calif.), and the Cre-ERT tamoxifen inducible recombinase system (Indra et al., *Nuc. Acid. Res.,* 27: 4324-4327 (1999); *Nuc. Acid. Res.,* 28: e99 (2000); U.S. Pat. No. 7,112,715; and Kramer & Fussenegger, *Methods Mol. Biol.,* 308: 123-144 (2005)).

A promoter can be selected by matching its particular pattern of activity with the desired pattern and level of expression of an antigen(s). For example, the adenoviral vector can comprise two or more nucleic acid sequences that encode different Dengue virus antigens and are operably linked to different promoters displaying distinct expression profiles. In this regard, a first promoter can be selected to mediate an initial peak of antigen production, thereby priming the immune system against an encoded antigen. A second promoter can be selected to drive production of the same or different antigen such that expression peaks several days after that of the first promoter, thereby "boosting" the immune system against the antigen. Alternatively, a hybrid promoter can be constructed which combines the desirable aspects of multiple promoters. In as much as antigens can be toxic to eukaryotic cells, it may be advantageous to modify the promoter to decrease activity in complementing cell lines used to propagate the adenoviral vector.

Multiple nucleic acid sequences can be operably linked to the same or different promoters. In a preferred embodiment of the invention, each Dengue virus antigen-encoding nucleic acid sequence is operably linked to a separate promoter. While it is preferred that each promoter is different, one or ordinary skill in the art will appreciate the advantages of using one particularly efficient promoter to control expression of each Dengue virus antigen-encoding nucleic acid sequence present in the adenoviral vector. Thus, each Dengue virus antigen-encoding nucleic acid sequence can be operably linked to the same promoter. Most preferably, each of the at least two Dengue virus antigen-encoding nucleic acid sequences are operably linked to a different promoter. For example, one Dengue virus antigen-encoding nucleic acid sequence can be operably linked to a human CMV (hCMV) promoter, while a second Dengue virus antigen-encoding nucleic acid sequence can be operably linked to a mouse CMV (mCMV) promoter. The selection of an appropriate promoter for a given Dengue virus antigen-encoding nucleic acid sequence will depend upon a number of factors, including promoter strength and the position of the Dengue virus antigen-encoding nucleic acid sequence within the adenoviral genome, and can be performed using routine methods known in the art.

To optimize protein production, preferably the antigen-encoding nucleic acid sequence further comprises a polyadenylation site following the coding sequence. Any suitable polyadenylation sequence can be used, including a synthetic optimized sequence, as well as, for example, the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Simian Virus-40) polyadenylation sequence. Also, preferably all the proper transcription signals (and translation signals, where appropriate) are correctly arranged such that the nucleic acid sequence is properly expressed in the cells into which it is introduced. If desired, the nucleic acid sequence also can incorporate splice sites (i.e., splice acceptor and splice donor sites) to facilitate mRNA production.

If the Dengue virus antigen-encoding nucleic acid sequence encodes a processed or secreted protein or peptide, or a protein that acts intracellularly, preferably the Dengue virus antigen-encoding nucleic acid sequence further comprises the appropriate sequences for processing, secretion, intracellular localization, and the like. The Dengue virus antigen-encoding nucleic acid sequence can be operably linked to a signal sequence, which targets a protein to cellular machinery for secretion. Appropriate signal sequences include, but are not limited to, leader sequences for immunoglobulin heavy chains and cytokines (see, for example, Ladunga et al., *Current Opinions in Biotechnology,* 11: 13-18 (2000)). Other protein modifications can be required to secrete a protein from a host cell, which can be determined using routine laboratory techniques. Preparing expression constructs encoding antigens and signal sequences is further described in, for example, U.S. Pat. No. 6,500,641. Methods of secreting non-secretable proteins are further described in, for example, U.S. Pat. No. 6,472,176, and International Patent Application Publication WO 2002/048377.

A Dengue virus antigen encoded by a nucleic acid sequence of the adenoviral vector also can be modified to attach or incorporate the antigen on a host cell surface. In this respect, the antigen can comprise a membrane anchor, such as a gpi-anchor, for conjugation onto a cell surface. A transmembrane domain can be fused to the antigen to incorporate a terminus of the antigen protein into the cell membrane. Other strategies for displaying peptides on a cell surface are known in the art and are appropriate for use in the context of the invention.

The invention provides a composition comprising at least one adenoviral vector as described herein and a carrier, such as a physiologically acceptable (e.g., pharmaceutically acceptable) carrier. Thus, the composition can be a pharmaceutical composition, which optionally can be sterile. Any suitable carrier can be used within the context of the invention, and such carriers are well known in the art. The choice of carrier will be determined, in part, by the particular site to which the composition is to be administered and the particular method used to administer the composition.

The composition can comprise a plurality of the adenoviral vectors described herein (e.g., 2, 3, 4, 5 or more adenoviral vectors). Preferably, the composition comprises two adenoviral vectors as described herein (desirably replication-deficient adenoviral vectors as described herein) and a pharmaceutically acceptable carrier, wherein (a) the first adenoviral vector comprises (i) a nucleic acid sequence encoding a serotype DV1 Dengue virus pre-membrane and envelope fusion protein and (ii) a nucleic acid sequence encoding a serotype DV3 Dengue virus pre-membrane and envelope fusion protein, and (b) the second adenoviral vector comprises (i) a nucleic acid sequence encoding a serotype DV2 Dengue virus pre-membrane and envelope fusion protein and (ii) a nucleic acid sequence encoding a serotype DV4 Dengue virus pre-membrane and envelope fusion protein. Descriptions of the adenoviral vectors, Dengue virus antigens, and promoters set forth above in connection with other embodiments of the invention also are applicable to those same aspects of the aforesaid composition.

A composition comprising one or more replication-deficient adenoviral vectors and a pharmaceutically acceptable carrier desirably is substantially free of replication-competent adenovirus (RCA) contamination (e.g., the composition comprises less than about 1% of replication-competent adenovirus on the basis of the total adenoviruses in the composition). Most desirably, the composition is RCA-free. Adenoviral vector compositions and stocks that are RCA-free are described in U.S. Pat. No. 5,944,106, and International Patent Application Publication WO 1995/034671.

The invention also provides a method of inducing an immune response against Dengue virus in a mammal. The method comprises administering to the mammal a composition described herein, whereupon each of the nucleic acid sequences encoding a Dengue virus antigen is expressed in the mammal to produce the Dengue virus antigens and thereby induce an immune response against Dengue virus. The one or more adenoviral vectors desirably are administered in the form of a physiologically acceptable (e.g., pharmaceutically acceptable) composition, which comprises a carrier, preferably a physiologically (e.g., pharmaceutically) acceptable carrier, and the adenoviral vector.

In the method of the invention, the adenoviral vector preferably is administered to a mammal (e.g., a mouse, rat, rabbit, non-human primate, or a human), wherein the nucleic acid sequences encoding the Dengue virus antigens are expressed to induce an immune response against the antigens in the mammal. In embodiments where multiple adenoviral vectors are administered to a mammal, the adenoviral vectors can be separately formulated and administered simultaneously or sequentially in any order. Alternatively, as discussed above, the adenoviral vectors can be part of the same pharmaceutical composition. The immune response can be a humoral immune response, a cell-mediated immune response, or, desirably, a combination of humoral and cell-mediated immunity. Ideally, the immune response provides protection upon subsequent challenge with a Dengue virus of any serotype. However, protective immunity is not required in the context of the invention. The inventive method further can be used for antibody production and harvesting in non-human mammals (e.g., rabbits or mice).

To enhance the immune response generated against a Dengue virus antigen, the composition also can comprise an immune stimulator, or a nucleic acid sequence that encodes an immune stimulator. Immune stimulators also are referred to in the art as "adjuvants," and include, for example, cytokines, chemokines, or chaperones. Cytokines include, for example, Macrophage Colony Stimulating Factor (e.g., GM-CSF), Interferon Alpha (IFN-$\alpha$), Interferon Beta (IFN-$\beta$), Interferon Gamma (IFN-$\gamma$), interleukins (IL-1, IL-2, IL-4, IL-5, IL-6, IL-8, IL-10, IL-12, IL-13, IL-15, IL-16, and IL-18), the TNF family of proteins, Intercellular Adhesion Molecule-1 (ICAM-1), Lymphocyte Function-Associated antigen-3 (LFA-3), B7-1, B7-2, FMS-related tyrosine kinase 3 ligand, (Flt3L), vasoactive intestinal peptide (VIP), and CD40 ligand. Chemokines include, for example, B Cell-Attracting chemokine-1 (BCA-1), Fractalkine, Melanoma Growth Stimulatory Activity protein (MGSA), Hemofiltrate CC chemokine 1 (HCC-1), Interleukin 8 (IL-8), Interferon-stimulated T-cell alpha chemoattractant (I-TAC), Lymphotactin, Monocyte Chemotactic Protein 1 (MCP-1), Monocyte Chemotactic Protein 3 (MCP-3), Monocyte Chemotactic Protein 4 (CP-4), Macrophage-Derived Chemokine (MDC), a macrophage inflammatory protein (MIP), Platelet Factor 4 (PF4), RANTES, BRAK, eotaxin, exodus 1-3, and the like. Chaperones include, for example, the heat shock proteins Hsp170, Hsc70, and Hsp40.

Suitable formulations for the composition include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenoviral vector is administered in a composition formulated to protect the adenoviral vector from damage prior to administration. For example, the composition can be formulated to reduce loss of the adenoviral vector on devices used to prepare, store, or administer the adenoviral vector, such as glassware, syringes, or needles. The composition can be formulated to decrease the light sensitivity and/or temperature sensitivity of the adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the vector, facilitate administration, and increase the efficiency of the inventive method. Formulations for adenoviral vector-containing compositions are further described in, for example, U.S. Pat. No. 6,225,289, U.S. Pat. No. 6,514,943, and International Patent Application Publication WO 2000/034444.

The composition also can be formulated to enhance transduction efficiency. In addition, one of ordinary skill in the art will appreciate that the adenoviral vector can be present in a composition with other therapeutic or biologically-active agents. For example, factors that control inflammation, such as ibuprofen or steroids, can be part of the composition to reduce swelling and inflammation associated with in vivo administration of the adenoviral vector. As discussed herein, immune system stimulators or adjuvants, e.g., interleukins, lipopolysaccharide, or double-stranded RNA, can be administered to enhance or modify any immune response to the Dengue virus antigen. Antibiotics, i.e., microbicides and fungicides, can be present to treat existing infection and/or reduce the risk of future infection, such as infection associated with gene transfer procedures.

Any route of administration can be used to deliver the composition to the mammal. Indeed, although more than one route can be used to administer the composition, a particular route can provide a more immediate and more effective reaction than another route. Preferably, the composition is administered via intramuscular injection or intranasal administration. The composition also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The adenoviral vector can be administered in or on a device that allows controlled or sustained release, such as a sponge, biocompatible meshwork, mechanical reservoir, or mechanical implant. Implants (see, e.g., U.S. Pat. No. 5,443,505) and devices (see, e.g., U.S. Pat. No. 4,863,457), such as an implantable device, e.g., a mechanical reservoir or an implant or a device comprised of a polymeric composition, are particularly useful for administration of the adenoviral vector. The adenoviral vector also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate BHET), and/or a polylactic-glycolic acid.

The dose of adenoviral vector administered to the mammal will depend on a number of factors, including the size of a target tissue, the extent of any side-effects, the particular route of administration, and the like. The dose ideally comprises an "effective amount" of adenoviral vector, i.e., a dose of adenoviral vector which provokes a desired immune response in the mammal. The desired immune response can entail production of antibodies, protection upon subsequent challenge, immune tolerance, immune cell activation, and the like. Preferably, the desired immune response results in sufficient immunity for the recipient for a desired period of time such that subsequent infection with any of the four Dengue virus serotypes does not result in Dengue fever, Dengue hemorrhagic fever, or Dengue shock syndrome. Without wishing to be bound by any particular theory, use of an adenoviral vector-based vaccine for Dengue virus may reduce the risk of developing symptoms associated with a Dengue virus infection, when compared with more traditional vaccines based on live attenuated or inactive Dengue virus.

Desirably, a single dose of adenoviral vector comprises about $1\times10^5$ or more particles (which also are referred to as particle units (pu)) of the adenoviral vector, e.g., about $1\times10^6$ or more particles, about $1\times10^7$ or more particles, about $1\times10^8$ or more particles, about $1\times10^9$ or more particles, or about $1\times10^{10}$ or more particles of the adenoviral vector. Alternatively, or in addition, a single dose of adenoviral vector comprises about $1\times10^{14}$ particles or less of the adenoviral vector, e.g., about $1\times10^{13}$ particles or less, about $1\times10^{12}$ particles or less, about $1\times10^{11}$ particles or less, about $1\times10^{10}$ particles or less, or about $1\times10^9$ particles or less of the adenoviral vector. Thus, a single dose of adenoviral vector can comprise a quantity of particles of the adenoviral vector in a range defined by any two of the aforementioned values. For example, a single dose of adenoviral vector can comprise $1\times10^5$-$1\times10^{14}$ particles, $1\times10^6$-$1\times10^{12}$ particles, $1\times10^8$-$1\times10^{11}$ particles, $1\times10^9$-$1\times10^{12}$ particles, $1\times10^9$-$1\times10^{11}$ particles, $1\times10^9$-$1\times10^{10}$ particles, or $1\times10^{10}$ -$1\times10^{12}$ particles, of the adenoviral vector. In other words, a single dose of adenoviral vector can comprise, for example, about $1\times10^6$ pu, $2\times10^6$ pu, $4\times10^6$ pu, $1\times10^7$ pu, $2\times10^7$ pu, $4\times10^7$ pu, $1\times10^8$ pu, $2\times10^8$ pu, $4\times10^8$ pu, $1\times10^9$ pu, $2\times10^9$ pu, $4\times10^9$ pu, $1\times10^{10}$ pu, $2\times10^{10}$ pu, $4\times10^{10}$ pu, $1\times10^{11}$ pu, $2\times10^{11}$ pu, $4\times10^{11}$ pu, $1\times10^{12}$ pu, $2\times10^{12}$ pu, or $4\times10^{12}$ pu of the adenoviral vector.

Administering the composition containing the adenoviral vector (or adenoviral vectors) encoding Dengue virus antigens can be one component of a multistep regimen for inducing an immune response against Dengue virus in a mammal. In particular, the inventive method can represent one arm of a prime and boost immunization regimen. In this respect, the method comprises administering to the mammal a boosting composition after administering the composition comprising the inventive adenoviral vector to the mammal. In this embodiment, therefore, the immune response is "primed" upon administration of the composition containing the inventive adenoviral vector, and is "boosted" upon administration of the boosting composition. Alternatively, the inventive method comprises administering to the mammal a priming composition to the mammal prior to administering the composition comprising the inventive adenoviral vector to the mammal. In this embodiment, therefore, the immune response is "primed" upon administration of the priming composition, and is "boosted" upon administration of the composition containing the inventive adenoviral vector.

The priming composition or the boosting composition that is not the inventive composition desirably comprises a gene transfer vector that comprises a nucleic acid sequence encoding a Dengue virus antigen. Any gene transfer vector can be employed, including viral and non-viral gene transfer vectors. Examples of suitable viral gene transfer vectors include, but are not limited to, retroviral vectors, adeno-associated virus vectors, vaccinia virus vectors, herpesvirus vectors, parainfluenza-RSV chimeric vectors (PIV-RSV), and adenoviral vectors. Examples of suitable non-viral vectors include, but are not limited to, plasmids, liposomes, and molecular conjugates (e.g., transferrin). Preferably, the priming composition or the boosting composition is a plasmid or an adenoviral vector. Alternatively, an immune response can be primed or boosted by administration of a Dengue virus protein itself (e.g., an antigenic Dengue virus protein) with or without a suitable adjuvant (e.g., alum, QS-21, insulin-derived adjuvant, etc.), a tetravalent attenuated dengue vaccine, a killed dengue virus, a live-attenuated Dengue virus particle, a virus-like particle, and the like. When the priming composition and/or the boosting composition is an adenoviral vector, it can be an adenoviral vector derived from any human or non-human animal as described herein. In a preferred embodiment, the priming composition and/or the boosting composition comprises a human adenoviral vector based on, e.g., human serotypes 5, 28, or 35, or a simian adenoviral vector based on, e.g., serotypes 7, 11, 16, or 38. For example, a priming composition containing a human serotype 28 adenoviral vector can be administered to a human, followed by administration of a boosting composition containing the inventive adenoviral vector. Alternatively, a priming composition containing the inventive adenoviral vector can be administered to a human, followed by administration of a boosting composition containing a human serotype 28 adenoviral vector. In another embodiment, a priming composition containing the inventive adenoviral vector described herein can be administered to a human, followed by a second administration of the same composition or a different composition that is in accordance with the invention. One of ordinary skill in the art will appreciate that any combination of adenoviral vectors encoding one or more Dengue virus antigens can be employed as the priming or boosting composition in conjunction with a composition comprising the adenoviral vector of the invention.

The gene transfer vector of the priming composition and the boosting composition desirably comprises at least one nucleic acid sequence encoding a Dengue virus antigen. The Dengue virus antigen encoded by the nucleic acid sequence of the priming composition and/or the boosting composition can be the same as one of the Dengue antigens encoded by the inventive adenoviral vector. Alternatively, the Dengue virus antigen encoded by the nucleic acid sequence of the priming composition and/or the boosting composition can be different from the Dengue virus antigen(s) encoded by the inventive adenoviral vector. In one embodiment, the gene transfer vector of the priming composition and/or the boosting composition comprises multiple (i.e., two or more) nucleic acid sequences encoding the same Dengue virus antigen. In another embodiment, the gene transfer vector of the priming composition and/or the boosting composition can comprise multiple nucleic acid sequences encoding two or more different Dengue virus antigens.

Administration of the priming composition and the boosting composition can be separated by any suitable timeframe, e.g., 1 week or more, 2 weeks or more, 4 weeks or more, 8 weeks or more, 12 weeks or more, 16 weeks or more, 24 weeks or more, 52 weeks or more, or a range defined by any two of the foregoing values. The boosting composition preferably is administered to a mammal (e.g., a human) 2 weeks or more (e.g., 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 20 weeks, 24 weeks, 28 weeks, 35 weeks, 40 weeks, 50 weeks, 52 weeks, or a range defined by any two of the foregoing values) following administration of the priming composition. More than one dose of priming composition and/or boosting composition can be provided in any suitable timeframe. The dose of the priming composition and boosting composition administered to the mammal depends on a number of factors, including the extent of any side-effects, the particular route of administration, and the like.

The following examples further illustrate the present invention and, of course, should not be construed as in any way limiting its scope.

Example 1

This example demonstrates the construction of an adenoviral vector comprising a chimeric hexon protein and multiple nucleic acid sequences each encoding a Dengue antigen.

E1/E3/E4-deleted adenoviral vectors based on a serotype 5 adenovirus were generated using the AdFAST™ homologous recombination system (GenVec, Inc., Gaithersburg, Md.; described in Brough et al., *J. Virol.*, 70: 6497-6501 (1996)). The adenoviral vectors were further engineered to contain a chimeric hexon protein, in which the Ad5 hypervariable regions were replaced with the hypervariable regions from a serotype 43 adenovirus, and the threonine residue at position 333 of the chimeric hexon protein was replaced with a methionine residue (i.e., a T333M mutation). One such adenoviral vector (AdH.D13) was further engineered to express the Dengue virus 1 (DV1) and DV3 PreM and envelope (prM&E) fusion proteins (DME1 and DME3). Expression of the DME1 and DME3 genes was under the control of the human and murine cytomegalovirus (CMV) promoters, respectively. The DME1 expression cassette was inserted into the E1 region, oriented from left to right with respect to the Ad5 genome, while the DME3 expression cassette was inserted into the E4 region, oriented from left to right with respect to the Ad5 genome.

A second adenoviral vector (AdH.D24) was engineered to express the DV2 and DV4 prM&E fusion proteins (DME2 and DME4). Expression of the DME2 and DME4 genes was under the control of the human and murine cytomegalovirus (CMV) promoters, respectively. The DME2 expression cassette was inserted into the E1 region, oriented from left to right with respect to the Ad5 genome, while the DME4 expression cassette was inserted into the E4 region, oriented from left to right with respect to the Ad5 genome.

The AdH.D13 and AdH.D24 vectors were produced on 293-ORF6 cells. The sequences of the vectors and DV antigens were confirmed by PCR and DNA sequencing. The AdH.D13 vector was confirmed to express DME1 and DME3 proteins in vitro using a Western blot assay. Specifically, 293 cells were infected with 500 particle units per cell of AdH.D13, and the cell monolayer was harvested 24 hours later in M-PER buffer (Thermo Scientific, Waltham, Mass.) with protease inhibitor to generate protein extracts. The protein extracts were mixed with NuPAGE LDS sample buffer (Life Technologies, Carlsbad, Calif.), according to the manufacturer's guidelines and heated at 70° C. for 5 minutes, then resolved at 200 constant volts for 50 minutes on a 4-12% NuPAGE Bis-Tris (Life Technologies, Carlsbad, Calif.) gel. The proteins were transferred to a polyvinylidene fluoride (PVDF) membrane (Life Technologies, Carlsbad, Calif.) for 70 minutes at 20 volts with a BioRad (Hercules, Calif.) semi-dry transfer apparatus. Membranes were blocked in blocking solution from the WesternBreeze Chemiluminescent Western Blot Immunodetection Kit (Life Technologies, Carlsbad, Calif.) for 30 minutes and probed with the appropriate anti-Dengue envelope monoclonal antibody (Dengue 1-4-specific antibodies were provided by the United States Navy). In this respect, the Dengue 1 primary antibody (clone 8B9 for Dengue 1 assay) and the Dengue 3 primary antibody (clone 16C7 for Dengue 3 assay) were diluted 1:10000 and 1:500, respectively, in blocking buffer (Life Technologies, Carlsbad, Calif.) and incubated for 1 hour at room temperature with rocking. The Dengue 2 primary antibody and the Dengue 4 primary antibody were diluted 1:500 in blocking buffer (Life Technologies, Carlsbad, Calif.) and incubated for 1 hour at room temperature with rocking. Membranes were washed four times for five minutes each in washing buffer (Life Technologies, Carlsbad Calif.) at room temperature followed by 30 minutes incubation with Alkaline Phosphatase-conjugated secondary anti-mouse antibody solution (Life Technologies, Carlsbad Calif.) with rocking, and developed with chemiluminescent substrate CDP Star (Life Technologies, Carlsbad Calif.).

For AdH.D13, the Western blot yielded reactive proteins that migrated to the position of approximately 55 KDa. The molecular weight of the DME1 protein expressed from AdH.D13 was indistinguishable from that observed following transfection of the positive control plasmid AdH.D13 into 293 cells, as well as from the cell lysate from infection of Vero cells by the positive Dengue 1 virus. The molecular weight of the DME3 protein expressed from AdH.D13 was indistinguishable from that observed following infection of Vero cells by the positive Dengue 3 virus.

For AdH.D24, the Western blot assay yielded reactive proteins that migrated to the position of approximately 50-55 KDa. The molecular weight of the Dengue 2 protein expressed from AdH.D24 was slightly different from that observed following infection of Vero cells by the positive Dengue 2 virus, which may be due to a difference in glycosylation in Vero cells versus 293 cells. The molecular weight of the DME2 protein expressed from AdH.D24 was indistinguishable from that observed following transfection of the Dengue 2-expressing positive control plasmid into 293 cells. The DME4 protein expressed from AdH.D24 was detected by an immunofluorescence assay in 293 cells infected with the AdH.D24 vector. Infection of Vero cells by the positive Dengue 4 virus also showed expression of DME4 in this analysis, and the AdH.D13 vector was negative for DME4 expression in this assay.

The results of this example demonstrates the production of replication-deficient adenoviral vectors in accordance with the invention.

Example 2

This example demonstrates that the adenoviral vectors of the invention induce an immune response against Dengue virus in mice.

Mice were immunized with an Ad5 vector that does not contain a transgene (AdNull), or a mixture of equal parts of AdH.D13 and AdH.D24 (described in Example 1), via intramuscular (IM) administration. Four weeks later, the mice were bled, and serum was tested for Dengue-specific antibodies using an ELISA assay. Serum was diluted 1:100 and added to wells pre-coated with either D1, D2, D3, or D4 envelope protein. After washing and incubation with secondary antibody, the plates were read in a plate reader. The figure shows that no Dengue-specific antibody was detected in mice immunized with AdNull. However, antibodies that reacted against all four dengue envelope antigens were detected in mice immunized with the mixture of the two adenoviral vectors which collectively expressed D1, D2, D3, and D4 preM and envelope fusion proteins.

The results of this example demonstrate that a combination of bivalent adenoviral vectors expressing Dengue virus preM and envelope fusion proteins induces humoral immune responses in mice.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The Willis "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A replication-deficient adenoviral vector comprising two or more of the following:

(a) the nucleic acid sequence of SEQ ID NO: 7, which encodes a serotype DV1 Dengue virus pre-membrane and envelope fusion protein, (b) the nucleic acid sequence of SEQ ID NO: 8, which encodes a serotype DV2 Dengue virus pre-membrane and envelope fusion protein, (c) the nucleic acid sequence of SEQ ID NO: 9, which encodes a serotype DV3 Dengue virus pre-membrane and envelope fusion protein, or (d) the nucleic acid sequence of SEQ ID NO: 10, which encodes a serotype DV4 Dengue virus pre-membrane and envelope fusion protein.

2. The adenoviral vector of claim 1, wherein the adenoviral vector requires complementation of a deficiency in the E1A region, the E1B region, and/or the E4 region of the adenoviral genome for propagation.

3. The adenoviral vector of claim 2, wherein the adenoviral vector requires complementation of a deficiency in the E1A region and the E1B region of the adenoviral genome for propagation.

4. The adenoviral vector of claim 2, wherein the adenoviral vector requires complementation of a deficiency in the E1A region, the E1B region, and the E4 region of the adenoviral genome for propagation.

5. The adenoviral vector of claim 4, wherein the adenoviral genome lacks the entire E1 region and at least a portion of the E4 region.

6. The adenoviral vector of claim 5, wherein at least one of the nucleic acid sequences is positioned in the deleted E1 region and at least one of the nucleic acid sequences is positioned in the deleted E4 region of the adenoviral genome.

7. The adenoviral vector of claim 1, which comprises a deficiency in the E3 region of the adenoviral genome.

8. A composition comprising the replication-deficient adenoviral vector of claim 1, and a pharmaceutically acceptable carrier.

9. A composition comprising two replication-deficient adenoviral vectors and a pharmaceutically acceptable carrier, wherein:

(a) the first adenoviral vector comprises (i) the nucleic acid sequence of SEQ ID NO: 7 and (ii) the nucleic acid sequence of SEQ ID NO: 9, and (b) the second adenoviral vector comprises (i) the nucleic acid sequence of SEQ ID NO: 8 and (ii) the nucleic acid sequence of SEQ ID NO: 10.

10. A method of inducing an immune response against Dengue virus in a mammal, which comprises administering to the mammal the composition of claim 8, whereupon each of the nucleic acid sequences encoding a Dengue virus antigen is expressed in the mammal to produce the Dengue virus antigens and wherein the composition is delivered in a sufficient amount to thereby induce an immune response against Dengue virus.

11. The method of claim 10, wherein the method comprises administering a priming composition to the mammal prior to administering the composition comprising the adenoviral vector to the mammal.

12. The method of claim 10, wherein the method comprises administering a boosting composition to the mammal after administering the composition comprising the adenoviral vector to the mammal.

13. A method of inducing an immune response against Dengue virus in a mammal, which comprises administering to the mammal the composition of claim 9, whereupon each of the nucleic acid sequences encoding a Dengue virus antigen is expressed in the mammal to produce the Dengue virus antigens and wherein the composition is delivered in a sufficient amount to thereby induce an immune response against Dengue virus.

14. The adenoviral vector of claim 1, which comprises the nucleic acid sequence of SEQ ID NO: 7 and the nucleic acid sequence of SEQ ID NO: 9.

15. The adenoviral vector of claim 1, which comprises the nucleic acid sequence of SEQ ID NO: 8 and the nucleic acid sequence of SEQ ID NO: 10.

16. The adenoviral vector of claim 1, which comprises the nucleic acid sequence of SEQ ID NO: 7 and the nucleic acid sequence of SEQ ID NO: 8.

17. The adenoviral vector of claim 1, which comprises the nucleic acid sequence of SEQ ID NO: 7 and the nucleic acid sequence of SEQ ID NO: 10.

18. The adenoviral vector of claim 1, which comprises the nucleic acid sequence of SEQ ID NO: 8 and the nucleic acid sequence of SEQ ID NO: 9.

19. The adenoviral vector of claim 1, which comprises the nucleic acid sequence of SEQ ID NO: 9 and the nucleic acid sequence of SEQ ID NO: 10.

20. The adenoviral vector of claim 1, which comprises (a) the nucleic acid sequence of SEQ ID NO: 7, (b) the nucleic acid sequence of SEQ ID NO: 8, (c) the nucleic acid sequence of SEQ ID NO: 9, and (d) the nucleic acid sequence of SEQ ID NO: 10.

* * * * *

SEQUENCE LISTING

```
<160> NUMBER OF SEQ ID NOS: 10

<210> SEQ ID NO 1
<211> LENGTH: 952
<212> TYPE: PRT
<213> ORGANISM: Adenovirus

<400> SEQUENCE: 1

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175
```

-continued

```
Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Thr Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Leu Asp Ser Ile Gly Asp Arg Thr Arg Tyr Phe
    370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Gly Gly Val Ile Asn Thr Glu Thr Leu Thr Lys Val Lys Pro Lys
            420                 425                 430

Thr Gly Gln Glu Asn Gly Trp Glu Lys Asp Ala Thr Glu Phe Ser Asp
        435                 440                 445

Lys Asn Glu Ile Arg Val Gly Asn Asn Phe Ala Met Glu Ile Asn Leu
    450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
            500                 505                 510

Leu Val Asp Cys Tyr Ile Asn Leu Gly Ala Arg Trp Ser Leu Asp Tyr
        515                 520                 525

Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
                565                 570                 575

Gly Ser Tyr Thr Tyr Glu Trp Asn Phe Arg Lys Asp Val Asn Met Val
            580                 585                 590
```

```
Leu Gln Ser Ser Leu Gly Asn Asp Leu Arg Val Asp Gly Ala Ser Ile
        595                 600                 605

Lys Phe Asp Ser Ile Cys Leu Tyr Ala Thr Phe Phe Pro Met Ala His
    610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
        675                 680                 685

Pro Ser Leu Gly Ser Gly Tyr Asp Pro Tyr Tyr Thr Tyr Ser Gly Ser
    690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
    770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Tyr
        835                 840                 845

Pro Leu Ile Gly Lys Thr Ala Val Asp Ser Ile Thr Gln Lys Lys Phe
    850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Phe Asp Val Val Arg Val
        915                 920                 925

His Arg Pro His Arg Gly Val Ile Glu Thr Val Tyr Leu Arg Thr Pro
    930                 935                 940

Phe Ser Ala Gly Asn Ala Thr Thr
945                 950
```

<210> SEQ ID NO 2
<211> LENGTH: 940
<212> TYPE: PRT
<213> ORGANISM: Artificial Sequence
<220> FEATURE:
<223> OTHER INFORMATION: Synthetic -continued

<400> SEQUENCE: 2

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Glu Thr Lys Glu Lys Gln Asn Gly Gly
    130                 135                 140

Ser Gly Ala Gln Ile Glu Lys Asn Val Thr His Val Phe Gly Gln Ala
145                 150                 155                 160

Pro Tyr Ser Gly Ile Asn Ile Thr Lys Glu Gly Ile Gln Ile Gly Val
                165                 170                 175

Glu Glu Ile Asn Asn Val Glu Glu Pro Lys Tyr Ala Asp Lys Thr Phe
            180                 185                 190

Gln Pro Glu Pro Gln Ile Gly Glu Ser Gln Trp Gln Glu Thr Phe Asn
        195                 200                 205

Phe Ala Ala Gly Arg Val Leu Lys Lys Thr Thr Pro Met Lys Pro Cys
    210                 215                 220

Tyr Gly Ser Tyr Ala Lys Pro Thr Asn Glu Asn Gly Gly Gln Gly Ile
225                 230                 235                 240

Leu Val Gly Glu Asn Val Asp Pro Thr Lys Glu Ser Gln Val Glu Met
                245                 250                 255

Gln Phe Phe Ser Thr Thr Gln Thr Asp Thr Gly Thr Thr Gln Leu Thr
            260                 265                 270

Pro Lys Val Val Leu Tyr Ser Glu Asp Val Asp Ile Glu Thr Pro Asp
        275                 280                 285

Thr His Ile Ser Tyr Met Pro Gly Lys Glu Asp Ala Ser Ser Arg Glu
    290                 295                 300

Leu Met Gly Gln Gln Ser Met Pro Asn Arg Pro Asn Tyr Ile Ala Phe
305                 310                 315                 320

Arg Asp Asn Phe Ile Gly Leu Met Tyr Tyr Asn Ser Thr Gly Asn Met
                325                 330                 335

Gly Val Leu Ala Gly Gln Ala Ser Gln Leu Asn Ala Val Val Asp Leu
            340                 345                 350

Gln Asp Arg Asn Thr Glu Leu Ser Tyr Gln Leu Leu Leu Asp Ser Ile
        355                 360                 365

Gly Asp Arg Thr Arg Tyr Phe Ser Met Trp Asn Gln Ala Val Asp Ser
    370                 375                 380

Tyr Asp Pro Asp Val Arg Ile Ile Glu Asn His Gly Thr Glu Asp Glu
385                 390                 395                 400

Leu Pro Asn Tyr Cys Phe Pro Leu Asp Gly Met Gly Ser Asn Ala Ala
                405                 410                 415
```

-continued

```
Tyr Gln Gly Val Lys Pro Lys Thr Gly Asn Gly Trp Asp Pro Asn Thr
            420                 425                 430

Asp Val Ala Ala Gln Asn Gln Ile Arg Val Gly Asn Asn Phe Ala Met
        435                 440                 445

Glu Ile Asn Leu Asn Ala Asn Leu Trp Arg Asn Phe Leu Tyr Ser Asn
    450                 455                 460

Ile Ala Leu Tyr Leu Pro Asp Lys Leu Lys Tyr Ser Pro Ser Asn Val
465                 470                 475                 480

Lys Ile Ser Asp Asn Pro Asn Thr Tyr Asp Tyr Met Asn Lys Arg Val
                485                 490                 495

Val Ala Pro Gly Leu Val Asp Cys Tyr Ile Asn Leu Gly Ala Arg Trp
            500                 505                 510

Ser Leu Asp Tyr Met Asp Asn Val Asn Pro Phe Asn His His Arg Asn
        515                 520                 525

Ala Gly Leu Arg Tyr Arg Ser Met Leu Leu Gly Asn Gly Arg Tyr Val
    530                 535                 540

Pro Phe His Ile Gln Val Pro Gln Lys Phe Phe Ala Ile Lys Asn Leu
545                 550                 555                 560

Leu Leu Leu Pro Gly Ser Tyr Thr Tyr Glu Trp Asn Phe Arg Lys Asp
                565                 570                 575

Val Asn Met Val Leu Gln Ser Ser Leu Gly Asn Asp Leu Arg Val Asp
            580                 585                 590

Gly Ala Ser Ile Lys Phe Asp Ser Ile Cys Leu Tyr Ala Thr Phe Phe
        595                 600                 605

Pro Met Ala His Asn Thr Ala Ser Thr Leu Glu Ala Met Leu Arg Asn
    610                 615                 620

Asp Thr Asn Asp Gln Ser Phe Asn Asp Tyr Leu Ser Ala Ala Asn Met
625                 630                 635                 640

Leu Tyr Pro Ile Pro Ala Asn Ala Thr Asn Val Pro Ile Ser Ile Pro
                645                 650                 655

Ser Arg Asn Trp Ala Ala Phe Arg Gly Trp Ala Phe Thr Arg Leu Lys
            660                 665                 670

Thr Lys Glu Thr Pro Ser Leu Gly Ser Gly Tyr Asp Pro Tyr Tyr Thr
        675                 680                 685

Tyr Ser Gly Ser Ile Pro Tyr Leu Asp Gly Thr Phe Tyr Leu Asn His
    690                 695                 700

Thr Phe Lys Lys Val Ala Ile Thr Phe Asp Ser Ser Val Ser Trp Pro
705                 710                 715                 720

Gly Asn Asp Arg Leu Leu Thr Pro Asn Glu Phe Glu Ile Lys Arg Ser
                725                 730                 735

Val Asp Gly Glu Gly Tyr Asn Val Ala Gln Cys Asn Met Thr Lys Asp
            740                 745                 750

Trp Phe Leu Val Gln Met Leu Ala Asn Tyr Asn Ile Gly Tyr Gln Gly
        755                 760                 765

Phe Tyr Ile Pro Glu Ser Tyr Lys Asp Arg Met Tyr Ser Phe Phe Arg
    770                 775                 780

Asn Phe Gln Pro Met Ser Arg Gln Val Val Asp Asp Thr Lys Tyr Lys
785                 790                 795                 800

Asp Tyr Gln Gln Val Gly Ile Leu His Gln His Asn Asn Ser Gly Phe
                805                 810                 815

Val Gly Tyr Leu Ala Pro Thr Met Arg Glu Gly Gln Ala Tyr Pro Ala
            820                 825                 830
```

```
Asn Phe Pro Tyr Pro Leu Ile Gly Lys Thr Ala Val Asp Ser Ile Thr
        835                 840                 845

Gln Lys Lys Phe Leu Cys Asp Arg Thr Leu Trp Arg Ile Pro Phe Ser
    850                 855                 860

Ser Asn Phe Met Ser Met Gly Ala Leu Thr Asp Leu Gly Gln Asn Leu
865                 870                 875                 880

Leu Tyr Ala Asn Ser Ala His Ala Leu Asp Met Thr Phe Glu Val Asp
                885                 890                 895

Pro Met Asp Glu Pro Thr Leu Leu Tyr Val Leu Phe Glu Val Phe Asp
            900                 905                 910

Val Val Arg Val His Gln Pro His Arg Gly Val Ile Glu Thr Val Tyr
        915                 920                 925

Leu Arg Thr Pro Phe Ser Ala Gly Asn Ala Thr Thr
    930                 935                 940


<210> SEQ ID NO 3
<211> LENGTH: 940
<212> TYPE: PRT
<213> ORGANISM: Artificial Sequence
<220> FEATURE:
<223> OTHER INFORMATION: Synthetic

<400> SEQUENCE: 3

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Glu Thr Lys Glu Lys Gln Asn Gly Gly
    130                 135                 140

Ser Gly Ala Gln Ile Glu Lys Asn Val Thr His Val Phe Gly Gln Ala
145                 150                 155                 160

Pro Tyr Ser Gly Ile Asn Ile Thr Lys Glu Gly Ile Gln Ile Gly Val
                165                 170                 175

Glu Glu Ile Asn Asn Val Glu Glu Pro Lys Tyr Ala Asp Lys Thr Phe
            180                 185                 190

Gln Pro Glu Pro Gln Ile Gly Glu Ser Gln Trp Gln Glu Thr Phe Asn
        195                 200                 205

Phe Ala Ala Gly Arg Val Leu Lys Lys Thr Thr Pro Met Lys Pro Cys
    210                 215                 220

Tyr Gly Ser Tyr Ala Lys Pro Thr Asn Glu Asn Gly Gly Gln Gly Ile
225                 230                 235                 240

Leu Val Gly Glu Asn Val Asp Pro Thr Lys Glu Ser Gln Val Glu Met
                245                 250                 255
```

-continued

```
Gln Phe Phe Ser Thr Thr Gln Thr Asp Thr Gly Thr Thr Gln Leu Thr
            260                 265                 270

Pro Lys Val Val Leu Tyr Ser Glu Asp Val Asp Ile Glu Thr Pro Asp
        275                 280                 285

Thr His Ile Ser Tyr Met Pro Gly Lys Glu Asp Ala Ser Ser Arg Glu
    290                 295                 300

Leu Met Gly Gln Gln Ser Met Pro Asn Arg Pro Asn Tyr Ile Ala Phe
305                 310                 315                 320

Arg Asp Asn Phe Ile Gly Leu Met Tyr Tyr Asn Ser Met Gly Asn Met
                325                 330                 335

Gly Val Leu Ala Gly Gln Ala Ser Gln Leu Asn Ala Val Val Asp Leu
            340                 345                 350

Gln Asp Arg Asn Thr Glu Leu Ser Tyr Gln Leu Leu Leu Asp Ser Ile
        355                 360                 365

Gly Asp Arg Thr Arg Tyr Phe Ser Met Trp Asn Gln Ala Val Asp Ser
    370                 375                 380

Tyr Asp Pro Asp Val Arg Ile Ile Glu Asn His Gly Thr Glu Asp Glu
385                 390                 395                 400

Leu Pro Asn Tyr Cys Phe Pro Leu Asp Gly Met Gly Ser Asn Ala Ala
                405                 410                 415

Tyr Gln Gly Val Lys Pro Lys Thr Gly Asn Gly Trp Asp Pro Asn Thr
            420                 425                 430

Asp Val Ala Ala Gln Asn Gln Ile Arg Val Gly Asn Asn Phe Ala Met
        435                 440                 445

Glu Ile Asn Leu Asn Ala Asn Leu Trp Arg Asn Phe Leu Tyr Ser Asn
    450                 455                 460

Ile Ala Leu Tyr Leu Pro Asp Lys Leu Lys Tyr Ser Pro Ser Asn Val
465                 470                 475                 480

Lys Ile Ser Asp Asn Pro Asn Thr Tyr Asp Tyr Met Asn Lys Arg Val
                485                 490                 495

Val Ala Pro Gly Leu Val Asp Cys Tyr Ile Asn Leu Gly Ala Arg Trp
            500                 505                 510

Ser Leu Asp Tyr Met Asp Asn Val Asn Pro Phe Asn His His Arg Asn
        515                 520                 525

Ala Gly Leu Arg Tyr Arg Ser Met Leu Leu Gly Asn Gly Arg Tyr Val
    530                 535                 540

Pro Phe His Ile Gln Val Pro Gln Lys Phe Phe Ala Ile Lys Asn Leu
545                 550                 555                 560

Leu Leu Leu Pro Gly Ser Tyr Thr Tyr Glu Trp Asn Phe Arg Lys Asp
                565                 570                 575

Val Asn Met Val Leu Gln Ser Ser Leu Gly Asn Asp Leu Arg Val Asp
            580                 585                 590

Gly Ala Ser Ile Lys Phe Asp Ser Ile Cys Leu Tyr Ala Thr Phe Phe
        595                 600                 605

Pro Met Ala His Asn Thr Ala Ser Thr Leu Glu Ala Met Leu Arg Asn
    610                 615                 620

Asp Thr Asn Asp Gln Ser Phe Asn Asp Tyr Leu Ser Ala Ala Asn Met
625                 630                 635                 640

Leu Tyr Pro Ile Pro Ala Asn Ala Thr Asn Val Pro Ile Ser Ile Pro
                645                 650                 655

Ser Arg Asn Trp Ala Ala Phe Arg Gly Trp Ala Phe Thr Arg Leu Lys
            660                 665                 670
```

```
Thr Lys Glu Thr Pro Ser Leu Gly Ser Gly Tyr Asp Pro Tyr Tyr Thr
        675                 680                 685

Tyr Ser Gly Ser Ile Pro Tyr Leu Asp Gly Thr Phe Tyr Leu Asn His
    690                 695                 700

Thr Phe Lys Lys Val Ala Ile Thr Phe Asp Ser Ser Val Ser Trp Pro
705                 710                 715                 720

Gly Asn Asp Arg Leu Leu Thr Pro Asn Glu Phe Glu Ile Lys Arg Ser
                725                 730                 735

Val Asp Gly Glu Gly Tyr Asn Val Ala Gln Cys Asn Met Thr Lys Asp
            740                 745                 750

Trp Phe Leu Val Gln Met Leu Ala Asn Tyr Asn Ile Gly Tyr Gln Gly
        755                 760                 765

Phe Tyr Ile Pro Glu Ser Tyr Lys Asp Arg Met Tyr Ser Phe Phe Arg
    770                 775                 780

Asn Phe Gln Pro Met Ser Arg Gln Val Val Asp Asp Thr Lys Tyr Lys
785                 790                 795                 800

Asp Tyr Gln Gln Val Gly Ile Leu His Gln His Asn Asn Ser Gly Phe
                805                 810                 815

Val Gly Tyr Leu Ala Pro Thr Met Arg Glu Gly Gln Ala Tyr Pro Ala
            820                 825                 830

Asn Phe Pro Tyr Pro Leu Ile Gly Lys Thr Ala Val Asp Ser Ile Thr
        835                 840                 845

Gln Lys Lys Phe Leu Cys Asp Arg Thr Leu Trp Arg Ile Pro Phe Ser
    850                 855                 860

Ser Asn Phe Met Ser Met Gly Ala Leu Thr Asp Leu Gly Gln Asn Leu
865                 870                 875                 880

Leu Tyr Ala Asn Ser Ala His Ala Leu Asp Met Thr Phe Glu Val Asp
                885                 890                 895

Pro Met Asp Glu Pro Thr Leu Leu Tyr Val Leu Phe Glu Val Phe Asp
            900                 905                 910

Val Val Arg Val His Gln Pro His Arg Gly Val Ile Glu Thr Val Tyr
        915                 920                 925

Leu Arg Thr Pro Phe Ser Ala Gly Asn Ala Thr Thr
    930                 935                 940


<210> SEQ ID NO 4
<211> LENGTH: 947
<212> TYPE: PRT
<213> ORGANISM: Artificial Sequence
<220> FEATURE:
<223> OTHER INFORMATION: Synthetic

<400> SEQUENCE: 4

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95
```

-continued

```
Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Glu Glu Lys Lys Asn Gly Gly Gly Ser
    130                 135                 140

Asp Ala Asn Gln Met Gln Thr His Val Phe Gly Gln Ala Pro Tyr Ser
145                 150                 155                 160

Gly Ile Asn Ile Thr Lys Glu Gly Ile Gln Ile Gly Ile Asp Ala Thr
                165                 170                 175

Lys Glu Glu Asp Asn Gly Lys Glu Ile Tyr Ala Asp Lys Thr Phe Gln
            180                 185                 190

Pro Glu Pro Gln Ile Gly Glu Ser Gln Trp Gln Asp Ser Asp Asn Tyr
        195                 200                 205

Tyr Gly Gly Arg Val Leu Lys Lys Thr Thr Pro Met Lys Pro Cys Tyr
    210                 215                 220

Gly Ser Tyr Ala Lys Pro Thr Asn Glu Asn Gly Gly Gln Ala Lys Phe
225                 230                 235                 240

Lys Thr Pro Glu Lys Glu Gly Glu Glu Pro Lys Glu Ser Gln Val Glu
                245                 250                 255

Met Gln Phe Phe Asp Ile Pro Ser Thr Gly Thr Gly Gly Asn Gly Thr
            260                 265                 270

Asn Val Asn Phe Lys Pro Lys Val Val Leu Tyr Ser Glu Asp Val Asp
        275                 280                 285

Ile Glu Thr Pro Asp Thr His Ile Ser Tyr Met Pro Gly Lys Glu Asp
    290                 295                 300

Ala Ser Ser Arg Glu Leu Met Gly Gln Gln Ser Met Pro Asn Arg Pro
305                 310                 315                 320

Asn Tyr Ile Ala Phe Arg Asp Asn Phe Ile Gly Leu Met Tyr Tyr Asn
                325                 330                 335

Ser Thr Gly Asn Met Gly Val Leu Ala Gly Gln Ala Ser Gln Leu Asn
            340                 345                 350

Ala Val Val Asp Leu Gln Asp Arg Asn Thr Glu Leu Ser Tyr Gln Leu
        355                 360                 365

Leu Leu Asp Ser Ile Gly Asp Arg Thr Arg Tyr Phe Ser Met Trp Asn
    370                 375                 380

Gln Ala Val Asp Ser Tyr Asp Pro Asp Val Arg Ile Ile Glu Asn His
385                 390                 395                 400

Gly Thr Glu Asp Glu Leu Pro Asn Tyr Cys Phe Pro Leu Asp Gly Ala
                405                 410                 415

Gly Thr Asn Ala Val Tyr Gln Gly Val Lys Val Lys Thr Thr Asn Asn
            420                 425                 430

Thr Glu Trp Glu Lys Asp Thr Ala Val Ser Glu His Asn Gln Ile Arg
        435                 440                 445

Val Gly Asn Asn Phe Ala Met Glu Ile Asn Leu Asn Ala Asn Leu Trp
    450                 455                 460

Arg Asn Phe Leu Tyr Ser Asn Ile Ala Leu Tyr Leu Pro Asp Lys Leu
465                 470                 475                 480

Lys Tyr Ser Pro Ser Asn Val Lys Ile Ser Asp Asn Pro Asn Thr Tyr
                485                 490                 495

Asp Tyr Met Asn Lys Arg Val Val Ala Pro Gly Leu Val Asp Cys Tyr
            500                 505                 510
```

-continued

Ile Asn Leu Gly Ala Arg Trp Ser Leu Asp Tyr Met Asp Asn Val Asn
515 520 525

Pro Phe Asn His His Arg Asn Ala Gly Leu Arg Tyr Arg Ser Met Leu
530 535 540

Leu Gly Asn Gly Arg Tyr Val Pro Phe His Ile Gln Val Pro Gln Lys
545 550 555 560

Phe Phe Ala Ile Lys Asn Leu Leu Leu Leu Pro Gly Ser Tyr Thr Tyr
565 570 575

Glu Trp Asn Phe Arg Lys Asp Val Asn Met Val Leu Gln Ser Ser Leu
580 585 590

Gly Asn Asp Leu Arg Val Asp Gly Ala Ser Ile Lys Phe Asp Ser Ile
595 600 605

Cys Leu Tyr Ala Thr Phe Phe Pro Met Ala His Asn Thr Ala Ser Thr
610 615 620

Leu Glu Ala Met Leu Arg Asn Asp Thr Asn Asp Gln Ser Phe Asn Asp
625 630 635 640

Tyr Leu Ser Ala Ala Asn Met Leu Tyr Pro Ile Pro Ala Asn Ala Thr
645 650 655

Asn Val Pro Ile Ser Ile Pro Ser Arg Asn Trp Ala Ala Phe Arg Gly
660 665 670

Trp Ala Phe Thr Arg Leu Lys Thr Lys Glu Thr Pro Ser Leu Gly Ser
675 680 685

Gly Tyr Asp Pro Tyr Tyr Thr Tyr Ser Gly Ser Ile Pro Tyr Leu Asp
690 695 700

Gly Thr Phe Tyr Leu Asn His Thr Phe Lys Lys Val Ala Ile Thr Phe
705 710 715 720

Asp Ser Ser Val Ser Trp Pro Gly Asn Asp Arg Leu Leu Thr Pro Asn
725 730 735

Glu Phe Glu Ile Lys Arg Ser Val Asp Gly Glu Gly Tyr Asn Val Ala
740 745 750

Gln Cys Asn Met Thr Lys Asp Trp Phe Leu Val Gln Met Leu Ala Asn
755 760 765

Tyr Asn Ile Gly Tyr Gln Gly Phe Tyr Ile Pro Glu Ser Tyr Lys Asp
770 775 780

Arg Met Tyr Ser Phe Phe Arg Asn Phe Gln Pro Met Ser Arg Gln Val
785 790 795 800

Val Asp Asp Thr Lys Tyr Lys Asp Tyr Gln Gln Val Gly Ile Leu His
805 810 815

Gln His Asn Asn Ser Gly Phe Val Gly Tyr Leu Ala Pro Thr Met Arg
820 825 830

Glu Gly Gln Ala Tyr Pro Ala Asn Phe Pro Tyr Pro Leu Ile Gly Lys
835 840 845

Thr Ala Val Asp Ser Ile Thr Gln Lys Lys Phe Leu Cys Asp Arg Thr
850 855 860

Leu Trp Arg Ile Pro Phe Ser Ser Asn Phe Met Ser Met Gly Ala Leu
865 870 875 880

Thr Asp Leu Gly Gln Asn Leu Leu Tyr Ala Asn Ser Ala His Ala Leu
885 890 895

Asp Met Thr Phe Glu Val Asp Pro Met Asp Glu Pro Thr Leu Leu Tyr
900 905 910

Val Leu Phe Glu Val Phe Asp Val Val Arg Val His Gln Pro His Arg
915 920 925

Gly Val Ile Glu Thr Val Tyr Leu Arg Thr Pro Phe Ser Ala Gly Asn
    930                 935                 940

Ala Thr Thr
945

<210> SEQ ID NO 5
<211> LENGTH: 947
<212> TYPE: PRT
<213> ORGANISM: Artificial Sequence
<220> FEATURE:
<223> OTHER INFORMATION: Synthetic

<400> SEQUENCE: 5

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Glu Glu Lys Lys Asn Gly Gly Gly Ser
    130                 135                 140

Asp Ala Asn Gln Met Gln Thr His Val Phe Gly Gln Ala Pro Tyr Ser
145                 150                 155                 160

Gly Ile Asn Ile Thr Lys Glu Gly Ile Gln Ile Gly Ile Asp Ala Thr
                165                 170                 175

Lys Glu Glu Asp Asn Gly Lys Glu Ile Tyr Ala Asp Lys Thr Phe Gln
            180                 185                 190

Pro Glu Pro Gln Ile Gly Glu Ser Gln Trp Gln Asp Ser Asp Asn Tyr
        195                 200                 205

Tyr Gly Gly Arg Val Leu Lys Lys Thr Thr Pro Met Lys Pro Cys Tyr
    210                 215                 220

Gly Ser Tyr Ala Lys Pro Thr Asn Glu Asn Gly Gly Gln Ala Lys Phe
225                 230                 235                 240

Lys Thr Pro Glu Lys Glu Gly Glu Glu Pro Lys Glu Ser Gln Val Glu
                245                 250                 255

Met Gln Phe Phe Asp Ile Pro Ser Thr Gly Thr Gly Gly Asn Gly Thr
            260                 265                 270

Asn Val Asn Phe Lys Pro Lys Val Val Leu Tyr Ser Glu Asp Val Asp
        275                 280                 285

Ile Glu Thr Pro Asp Thr His Ile Ser Tyr Met Pro Gly Lys Glu Asp
    290                 295                 300

Ala Ser Ser Arg Glu Leu Met Gly Gln Gln Ser Met Pro Asn Arg Pro
305                 310                 315                 320

Asn Tyr Ile Ala Phe Arg Asp Asn Phe Ile Gly Leu Met Tyr Tyr Asn
                325                 330                 335

-continued

```
Ser Met Gly Asn Met Gly Val Leu Ala Gly Gln Ala Ser Gln Leu Asn
            340                 345                 350

Ala Val Val Asp Leu Gln Asp Arg Asn Thr Glu Leu Ser Tyr Gln Leu
        355                 360                 365

Leu Leu Asp Ser Ile Gly Asp Arg Thr Arg Tyr Phe Ser Met Trp Asn
    370                 375                 380

Gln Ala Val Asp Ser Tyr Asp Pro Asp Val Arg Ile Ile Glu Asn His
385                 390                 395                 400

Gly Thr Glu Asp Glu Leu Pro Asn Tyr Cys Phe Pro Leu Asp Gly Ala
                405                 410                 415

Gly Thr Asn Ala Val Tyr Gln Gly Val Lys Val Lys Thr Thr Asn Asn
            420                 425                 430

Thr Glu Trp Glu Lys Asp Thr Ala Val Ser Glu His Asn Gln Ile Arg
        435                 440                 445

Val Gly Asn Asn Phe Ala Met Glu Ile Asn Leu Asn Ala Asn Leu Trp
    450                 455                 460

Arg Asn Phe Leu Tyr Ser Asn Ile Ala Leu Tyr Leu Pro Asp Lys Leu
465                 470                 475                 480

Lys Tyr Ser Pro Ser Asn Val Lys Ile Ser Asp Asn Pro Asn Thr Tyr
                485                 490                 495

Asp Tyr Met Asn Lys Arg Val Val Ala Pro Gly Leu Val Asp Cys Tyr
            500                 505                 510

Ile Asn Leu Gly Ala Arg Trp Ser Leu Asp Tyr Met Asp Asn Val Asn
        515                 520                 525

Pro Phe Asn His His Arg Asn Ala Gly Leu Arg Tyr Arg Ser Met Leu
    530                 535                 540

Leu Gly Asn Gly Arg Tyr Val Pro Phe His Ile Gln Val Pro Gln Lys
545                 550                 555                 560

Phe Phe Ala Ile Lys Asn Leu Leu Leu Leu Pro Gly Ser Tyr Thr Tyr
                565                 570                 575

Glu Trp Asn Phe Arg Lys Asp Val Asn Met Val Leu Gln Ser Ser Leu
            580                 585                 590

Gly Asn Asp Leu Arg Val Asp Gly Ala Ser Ile Lys Phe Asp Ser Ile
        595                 600                 605

Cys Leu Tyr Ala Thr Phe Phe Pro Met Ala His Asn Thr Ala Ser Thr
    610                 615                 620

Leu Glu Ala Met Leu Arg Asn Asp Thr Asn Asp Gln Ser Phe Asn Asp
625                 630                 635                 640

Tyr Leu Ser Ala Ala Asn Met Leu Tyr Pro Ile Pro Ala Asn Ala Thr
                645                 650                 655

Asn Val Pro Ile Ser Ile Pro Ser Arg Asn Trp Ala Ala Phe Arg Gly
            660                 665                 670

Trp Ala Phe Thr Arg Leu Lys Thr Lys Glu Thr Pro Ser Leu Gly Ser
        675                 680                 685

Gly Tyr Asp Pro Tyr Tyr Thr Tyr Ser Gly Ser Ile Pro Tyr Leu Asp
    690                 695                 700

Gly Thr Phe Tyr Leu Asn His Thr Phe Lys Lys Val Ala Ile Thr Phe
705                 710                 715                 720

Asp Ser Ser Val Ser Trp Pro Gly Asn Asp Arg Leu Leu Thr Pro Asn
                725                 730                 735

Glu Phe Glu Ile Lys Arg Ser Val Asp Gly Glu Gly Tyr Asn Val Ala
            740                 745                 750
```

-continued

Gln Cys Asn Met Thr Lys Asp Trp Phe Leu Val Gln Met Leu Ala Asn
755 760 765

Tyr Asn Ile Gly Tyr Gln Gly Phe Tyr Ile Pro Glu Ser Tyr Lys Asp
770 775 780

Arg Met Tyr Ser Phe Phe Arg Asn Phe Gln Pro Met Ser Arg Gln Val
785 790 795 800

Val Asp Asp Thr Lys Tyr Lys Asp Tyr Gln Gln Val Gly Ile Leu His
805 810 815

Gln His Asn Asn Ser Gly Phe Val Gly Tyr Leu Ala Pro Thr Met Arg
820 825 830

Glu Gly Gln Ala Tyr Pro Ala Asn Phe Pro Tyr Pro Leu Ile Gly Lys
835 840 845

Thr Ala Val Asp Ser Ile Thr Gln Lys Lys Phe Leu Cys Asp Arg Thr
850 855 860

Leu Trp Arg Ile Pro Phe Ser Ser Asn Phe Met Ser Met Gly Ala Leu
865 870 875 880

Thr Asp Leu Gly Gln Asn Leu Leu Tyr Ala Asn Ser Ala His Ala Leu
885 890 895

Asp Met Thr Phe Glu Val Asp Pro Met Asp Glu Pro Thr Leu Leu Tyr
900 905 910

Val Leu Phe Glu Val Phe Asp Val Val Arg Val His Gln Pro His Arg
915 920 925

Gly Val Ile Glu Thr Val Tyr Leu Arg Thr Pro Phe Ser Ala Gly Asn
930 935 940

Ala Thr Thr
945

<210> SEQ ID NO 6
<211> LENGTH: 950
<212> TYPE: PRT
<213> ORGANISM: Artificial Sequence
<220> FEATURE:
<223> OTHER INFORMATION: Synthetic

<400> SEQUENCE: 6

Met Ala Thr Pro Ser Met Met Pro Gln Trp Ser Tyr Met His Ile Ser
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Asn Asn Lys Phe Arg Asn Pro
35 40 45

Thr Val Ala Pro Thr His Asp Val Thr Thr Asp Arg Ser Gln Arg Leu
50 55 60

Thr Leu Arg Phe Ile Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Thr
100 105 110

Phe Lys Pro Tyr Ser Gly Thr Ala Tyr Asn Ala Leu Ala Pro Lys Gly
115 120 125

Ala Pro Asn Pro Cys Glu Trp Asp Glu Ala Ala Thr Ala Leu Glu Ile
130 135 140

Asn Leu Glu Glu Glu Asp Asp Asp Asn Glu Asp Glu Val Asp Glu Gln
145 150 155 160

-continued

```
Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Ala Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Leu Asp Ser Ile Gly Asp Arg Thr Arg Tyr Phe
    370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Asp Gly Val Gly Pro Gln Thr Asp Ser Tyr Lys Glu Ile Lys Pro
            420                 425                 430

Asn Gly Asp Gln Ser Thr Trp Thr Asn Val Asp Pro Asn Gly Ser Ser
        435                 440                 445

Gln Ile Arg Val Gly Asn Asn Phe Ala Met Glu Ile Asn Leu Asn Ala
    450                 455                 460

Asn Leu Trp Arg Asn Phe Leu Tyr Ser Asn Ile Ala Leu Tyr Leu Pro
465                 470                 475                 480

Asp Lys Leu Lys Tyr Ser Pro Ser Asn Val Lys Ile Ser Asp Asn Pro
                485                 490                 495

Asn Thr Tyr Asp Tyr Met Asn Lys Arg Val Val Ala Pro Gly Leu Val
            500                 505                 510

Asp Cys Tyr Ile Asn Leu Gly Ala Arg Trp Ser Leu Asp Tyr Met Asp
        515                 520                 525

Asn Val Asn Pro Phe Asn His His Arg Asn Ala Gly Leu Arg Tyr Arg
    530                 535                 540

Ser Met Leu Leu Gly Asn Gly Arg Tyr Val Pro Phe His Ile Gln Val
545                 550                 555                 560

Pro Gln Lys Phe Phe Ala Ile Lys Asn Leu Leu Leu Leu Pro Gly Ser
                565                 570                 575
```

```
Tyr Thr Tyr Glu Trp Asn Phe Arg Lys Asp Val Asn Met Val Leu Gln
            580                 585                 590

Ser Ser Leu Gly Asn Asp Leu Arg Val Asp Gly Ala Ser Ile Lys Phe
        595                 600                 605

Asp Ser Ile Cys Leu Tyr Ala Thr Phe Phe Pro Met Ala His Asn Thr
    610                 615                 620

Ala Ser Thr Leu Glu Ala Met Leu Arg Asn Asp Thr Asn Asp Gln Ser
625                 630                 635                 640

Phe Asn Asp Tyr Leu Ser Ala Ala Asn Met Leu Tyr Pro Ile Pro Ala
                645                 650                 655

Asn Ala Thr Asn Val Pro Ile Ser Ile Pro Ser Arg Asn Trp Ala Ala
            660                 665                 670

Phe Arg Gly Trp Ala Phe Thr Arg Leu Lys Thr Lys Glu Thr Pro Ser
        675                 680                 685

Leu Gly Ser Gly Tyr Asp Pro Tyr Tyr Thr Tyr Ser Gly Ser Ile Pro
    690                 695                 700

Tyr Leu Asp Gly Thr Phe Tyr Leu Asn His Thr Phe Lys Lys Val Ala
705                 710                 715                 720

Ile Thr Phe Asp Ser Ser Val Ser Trp Pro Gly Asn Asp Arg Leu Leu
                725                 730                 735

Thr Pro Asn Glu Phe Glu Ile Lys Arg Ser Val Asp Gly Glu Gly Tyr
            740                 745                 750

Asn Val Ala Gln Cys Asn Met Thr Lys Asp Trp Phe Leu Val Gln Met
        755                 760                 765

Leu Ala Asn Tyr Asn Ile Gly Tyr Gln Gly Phe Tyr Ile Pro Glu Ser
    770                 775                 780

Tyr Lys Asp Arg Met Tyr Ser Phe Phe Arg Asn Phe Gln Pro Met Ser
785                 790                 795                 800

Arg Gln Val Val Asp Asp Thr Lys Tyr Lys Asp Tyr Gln Gln Val Gly
                805                 810                 815

Ile Leu His Gln His Asn Asn Ser Gly Phe Val Gly Tyr Leu Ala Pro
            820                 825                 830

Thr Met Arg Glu Gly Gln Ala Tyr Pro Ala Asn Phe Pro Tyr Pro Leu
        835                 840                 845

Ile Gly Lys Thr Ala Val Asp Ser Ile Thr Gln Lys Lys Phe Leu Cys
    850                 855                 860

Asp Arg Thr Leu Trp Arg Ile Pro Phe Ser Ser Asn Phe Met Ser Met
865                 870                 875                 880

Gly Ala Leu Thr Asp Leu Gly Gln Asn Leu Leu Tyr Ala Asn Ser Ala
                885                 890                 895

His Ala Leu Asp Met Thr Phe Glu Val Asp Pro Met Asp Glu Pro Thr
            900                 905                 910

Leu Leu Tyr Val Leu Phe Glu Val Phe Asp Val Val Arg Val His Arg
        915                 920                 925

Pro His Arg Gly Val Ile Glu Thr Val Tyr Leu Arg Thr Pro Phe Ser
    930                 935                 940

Ala Gly Asn Ala Thr Thr
945                 950
```

<210> SEQ ID NO 7
<211> LENGTH: 2031
<212> TYPE: DNA
<213> ORGANISM: Artificial Sequence
<220> FEATURE:
<223> OTHER INFORMATION: Synthetic

<400> SEQUENCE: 7

```
atggcggtga ctatgttgtt gatgttgctt cctacggcgc tggcattcca cttgacaacg     60
agagggggtg agccccacat gatcgtgtcc aagcaagaga gggggaagtc gttgttgttt    120
aagacgtcag cgggggtgaa catgtgtaca ctgatcgcga tggacttggg cgagctttgc    180
gaggacacta tgacgtacaa gtgccctaga attaccgaaa cggagccgga tgacgtagat    240
tgctggtgca acgcgacaga gacatgggtc acttatggaa cgtgctcgca gactggggaa    300
catcgcaggg ataagagatc cgtagcgttg gcccctcacg tgggactcgg tcttgagact    360
aggatcgaaa cgtggatgtc gtcggaagga gcatggaagc agatccagaa agtggaaacg    420
tgggccctcc gccatccggg ttttacggtc atcgccctct ttctggcgca cgccattgga    480
acttcgatca cacaaaaagg gattatcttt atcctgctga tgctggtgac cccctcgatg    540
gctatgcgat gtgtcgggat tggcaaccgg gactttgtag aaggcctgtc cggagcaacg    600
tgggtagacg tggtgcttga acacggatca tgcgtcacga caatggcgaa agataaaccc    660
acactcgaca tcgagttgct caaaactgag gtgaccaacc cagcggtgtt gcgcaagctg    720
tgtatcgagg cgaagatttc caacaccact accgattcac ggtgccctac tcagggagag    780
gctacccttg tggaggaaca ggacactaac ttcgtctgta ggcgaacctt cgtagatagg    840
ggctggggga atggatgtgg gctgttcgga aaaggctcac tcatcacgtg cgctaagttc    900
aaatgcgtca caaaactgga agggaagatc gtccagtacg aaaatctgaa atactccgtg    960
attgtgaccg tgcacactgg ggatcagcac caggtgggaa acgaaacaac agagcatggg   1020
acaatcgcca cgattacacc acaagcgccc acctcagaaa ttcagctcac cgactatggt   1080
gcactgacgt tggactgttc accacgcaca gggctcgact tcaatgagat ggtcctcttg   1140
acgatggaaa agaaaagctg gctggtacat aaacagtggt ttctcgatct tccgctcccg   1200
tggacgagcg gagcctcgac gtcccaagaa acatggaata gacaggacct tttggtcacg   1260
ttcaaaacag cgcacgcgaa gaagcaggaa gtagtcgtgc ttggtagcca ggagggagcc   1320
atgcatacgg ccttgaccgg agctacagaa atccagacgt ccgggactac aaccatcttt   1380
gcgggacatc ttaagtgtcg gttgaagatg gataagctca cactcaaggg gatgtcgtac   1440
gtgatgtgca caggctcctt taagctcgaa aaagaggtgg cggaaacaca gcacgggacc   1500
gtccttgtgc aagtgaagta cgagggtact gacgcccctt gtaagatccc gttctcatcg   1560
caagacgaga agggagtcac gcaaaatgga cggctgatct cggcgaaccc cattgtcacg   1620
gataaggaga agccggtcaa tatcgaggca gagcctccct tcggagagtc ctacattgtc   1680
gtaggagcgg gtgagaaggc gctgaaactg agctggttca aaaaggggtc gtcaatcgga   1740
aagatgtttg aagccacggc ccgaggagca cggcggatgg caatcctcgg cgataccgct   1800
tgggacttcg gttcgattgg aggtgtattc actagcgtgg gcaaattgat ccaccaaatc   1860
tttggaacag cgtatggggt cttgttctcg ggagtgagct ggactatgaa aatcggcatt   1920
ggtattcttc tcacgtggct gggtcttaac tcaagatcga ccagcctttc aatgacgtgc   1980
attgccgtgg ggatggtaac gctctatttg ggtgtaatgg tgcaggcgtg a            2031
```

<210> SEQ ID NO 8
<211> LENGTH: 2019
<212> TYPE: DNA
<213> ORGANISM: Artificial Sequence
<220> FEATURE:
<223> OTHER INFORMATION: Synthetic

<400> SEQUENCE: 8
atggcgggaa tgatcattat gctgattccg actgtgatgg cttttcatct cacgacgcgg 60
aacggagaac cgcacatgat tgtgtcgcgc caggaaaagg gaaaatcgct gctgtttaag 120
actgaagatg gcgtaaacat gtgtaccctg atggcaatgg acctcgggga actgtgcgag 180
gacactatta cgtacaaatg ccctctcctt cgacagaatg agccagagga cattgactgt 240
tggtgcaaca gcacttcgac gtgggtaacc tatggtacat gcacgactac aggggaacac 300
cggagggaga agaggtcggt cgcgttggtg cctcacgtgg gaatgggcct cgaaacacgc 360
actgagacat ggatgtcgtc cgaaggcgca tggaagcacg cccaacgcat tgaaacatgg 420
attttgaggc accctggttt tacactcatg gcagtaatcc tcgcatatac aatcggaact 480
acacattttc agagagcttt gatcttcatc ctcctgacag ccgtagcgcc cagcatgacg 540
atgagatgca tcggcatctc aaatcgggat ttcgtggaag gtgtatcagg gggttcatgg 600
gtagacatcg tccttgagca tggttcgtgc gtcaccacaa tggcgaaaaa caagcctacc 660
cttgacttcg aactgatcaa gacggaggcg aaacagccgg ctacactcag aaagtactgt 720
attgaggcga aattgaccaa tacgacgaca gagtcgcggt gcccaaccca aggggagccc 780
tcccttaatg aggagcagga caaaaggttc gtatgcaagc attcaatggt cgatcggggc 840
tggggaaatg gatgtgggtt gtttggtaaa gggggaattg tgacgtgcgc gatgtttact 900
tgtaagaaga acatggaggg aaagatcgtg cagccggaga atttggaata cacaatcgtc 960
atcactccgc attcggggga agagcatgct gtcgggaacg acacagggaa acacggaaag 1020
gagatcaaga tcacgcccca atcaagcgtg acagaggcgg agcttactgg atacggcact 1080
gtgacgatgg agtgttcacc gagaaccgga ctcgatttca atgagatggt cctgcttcag 1140
atggagaata aggcgtggct ggtccaccga cagtggttct tggacctgcc ccttccctgg 1200
cttccgggtg ccgatacgca gggctcaaac tggattcaga aggaaaccct tgtcaccttc 1260
aagaacccgc acgcgaaaaa gcaggatgtg gtggtgctcg ggtcgcaaga aggtgcaatg 1320
catacggcgc ttacgggggc tacggagatt cagatgtcaa gcggcaatct tctcttcacc 1380
ggacatttga agtgcaggct gcgaatggac aaactgcaac ttaagggaat gtcctacagc 1440
atgtgtacag gcaaattcaa agtcgtcaaa gaaatcgccg agacacagca tgggaccatc 1500
gtagtcagag tgcagtatga aggggatggg tcgccatgca aaatcccctt ggagatcatg 1560
gacttggaaa agcgacacgt gcttggtagg ctcattacgg tgaaccccat tgtaacagaa 1620
aaagattcgc ccgtgaacat tgaagccgaa ccccctttcg gggactccta cgtaatcatc 1680
ggggtcgagc ccggacagct caaactcaac tggttcaaga aagggtcctc aatcggacaa 1740
atgtttgaaa cgacgatgcg gggagccaaa cgcatggcca ttctgggtga taccgcctgg 1800
gatttcggaa gccttggggg agtgtttacg tccattggaa aggcgctgca ccaagtattc 1860
ggagcaatct acggggcagc attcagcggt gtatcgtgga ctatggagtt tctgattcct 1920
attgccgtgg gtggagcgtt ggcgggattg gtgctcatcg tcctcatcgc gtatctgatc 1980
ggacggaagc gctcgcacgc cggttaccag acaatctga 2019

<210> SEQ ID NO 9
<211> LENGTH: 2025
<212> TYPE: DNA
<213> ORGANISM: Artificial Sequence
<220> FEATURE:
<223> OTHER INFORMATION: Synthetic

<400> SEQUENCE: 9
atggcttcgt tgtgtcttat gatgatgctt cccgctaccc ttgcatttca tctcacgtcc 60
cgagatggag aaccgcgcat gattgtcgga aagaacgaac gcgggaaatc gctgctcttc 120
aaaacagcat ccggaatcaa catgtgcacg ttgatcgcga tggatctcgg tgaaatgtgc 180
gatgataccg tcacatacaa atgtcctctc atcacggagg tcgagcccga ggacatcgac 240
tgttggtgta atcttacgtc aacttgggtc acgtatggta catgcaatca ggcgggagag 300
cacaggcgcg acaaacggtc agtggcgctc gctccacatg tcgggatggg tctggacacg 360
cgcactcaga catggatgtc agcagagggg gcgtggcggc aggtagagag agtcgagact 420
tgggcgtttc gacaccccgg ctttactatc cttgcgttgt ttttggcgca ttacatcggg 480
acgtcgctga cgcagaaggt agtcattttc atccttttga tgttggtcac tccgagcatg 540
actatgcggt gtgtgggcgt gggaaatcgg gacttcgtgg agggactctc gggtgccaca 600
tgggtagacg tagtccttga gcacggtggg tgcgtaacaa cgatggccaa gaacaagccg 660
acgttggata ttgaacttca gaaaacagaa gccacccagc tggcaacact taggaaactg 720
tgcattgaag ggaaaatcac aaacgtgacg acggacagca gatgtcccac ccagggggag 780
gcgattttgc ccgaagagca ggatcagaat tacgtgtgta aacacaccta cgtcgatcgc 840
ggttggggta atggttgcgg actctttggg aaggggtccc ttgtgacttg tgcgaaattc 900
caatgccttg agtccatcga ggggaaagtc gtgcaacacg agaacctcaa gtatacggtc 960
atcatcacgg tacacaccgg agatcaacat caggtcggaa acgagacaca gggagtaaca 1020
gcggaaatca cgccacaggc atccacggtg gaggcaatcc tccccgaata tggaacactc 1080
ggattggaat gctccccgag gactggtttg gacttcaacg aaatgattct gctcactatg 1140
aagaacaagg cgtggatggt gcacaggcag tggttcttcg acctgcctct gccttggacc 1200
tcaggggcca ccacagagac accgacttgg aacaaaaagg agttgctggt caccttcaag 1260
aatgctcatg ccaaaaagca agaggtggtg gtcttgggat cgcaagaagg ggcgatgcat 1320
acagcgctca cgggtgcgac cgagattcag accagcggtg gaacgagcat ctttgcgggt 1380
cacctcaagt gccggctcaa gatggacaaa ttggagctga aaggaatgag ctatgccatg 1440
tgcctgaatg cgtttgtgct gaagaaagaa gtctcggaga cacagcatgg aacgatcctt 1500
atcaaggtag aatacaaagg cgaagatgcc ccttgcaaga tccccttttag cacggaggat 1560 gggcagggaa aagcacacaa cgggagactc atcactgcca acccggtagt gaccaagaag 1620
gaggaaccgg tgaacatcga agccgaaccc ccattcggag aatcaaacat cgtgatcggt 1680
attggggaca aagcattgaa gatcaattgg tacaagaagg gatcgtcgat tgggaagatg 1740
ttcgaagcaa ccgcgagagg cgccagaagg atggcgatct tgggggacac cgcttgggac 1800
tttgggtcgg tagggggtgt actgaactcg ctgggaaaga tggtacatca gattttcggg 1860
tcggcctaca cggccctctt ttcgggagta tcgtggatta tgaagattgg gattggagtg 1920
ttgttgacat ggattggttt gaatagcaag aatacgtcca tgtcattctc atgcatcgtc 1980
atcggcatca ttacgctcta tcttggagtg gtggtccaag cataa 2025

<210> SEQ ID NO 10
<211> LENGTH: 2028
<212> TYPE: DNA
<213> ORGANISM: Artificial Sequence
<220> FEATURE:
<223> OTHER INFORMATION: Synthetic

<400> SEQUENCE: 10

```
atggctatta cattgctttg tctcatccct acggtcatgg cattccatct gccgactaga     60
gatggggagc cccttatgat tgtagggaaa cacgaaaggg gtcggccact cctcttcaaa    120
actacggagg gcatcaacaa gtgtactctc atcgctatgg atttgggcga aatgtgtgaa    180
gatactgtaa cgtataagtg tccccttctt gtaaacacgg aacccgagga cattgattgc    240
tggtgcaacc tgacctcggc ctgggtgatg tacgggacgt gcacgcagag cggcgagcgg    300
aggagagaga aacgcagcgt ggctcttact ccccactcgg gaatgggact ggaaacgcgc    360
gcagaaacgt ggatgtcgtc agagggagca tggaaacatg cgcagcgagt agagtcatgg    420
gtactccgca atcccggatt tgcactcctc gcggggttta tggcctacat gatcgggcag    480
accggcattc aacgggccgt attcttcgtc ctgatgatgc tcgtggcgcc gtcgtacgga    540
atgcggtgtg tgggggtcgg taaccgagat tttgtcgagg gagtaagcgg aggagcttgg    600
gtggatctgg tgctggaaca tggaggttgc gtgacgacga tggcgcaggg gaagccgacc    660
ttggatttcg aactcattaa gacaacagcg aaagaggtag cgcttcttcg gacttattgc    720
atcgaggcct caatttcgaa tatcacaacc gccacgagat gcccaacgca gggggagccg    780
tatttgaagg aagaacaaga ccagcagtac atttgtcggc gcgacgtggt ggacagggga    840
tggggtaacg ggtgcggact gttcggaaag ggagggggtag tcacgtgcgc caaattctca    900
tgctcgggga agatcaccgg taatctggta caaattgaaa acttggagta tacggtagtc    960
gtgacggtac ataacggaga tacacacgca gtggggaatg atacatccaa tcatggggtg   1020
acagcaacta tcacaccccg atccccctcg gtcgaagtga agttgcctga ttacggggaa   1080
ttgaccctcg attgtgagcc tcgatcgggc atcgacttta acgagatgat ccttatgaag   1140
atgaagaaga aaacgtggtt ggtccataag cagtggtttc tggaccttcc gctgccgtgg   1200
gctgccggtg cggatacatc cgaagtgcac tggaattaca aggaacggat ggtgactttc   1260
aaagtccccc atgcgaagcg ccaggacgtc acggtcctcg ggagccaaga aggtgccatg   1320
cactcggcct tgaccggagc gacagaggtg gactccgggg acggaaacca catgtttgcc   1380
gggcacttga aatgtaaagt gagaatggaa aaactgcgaa tcaaggggat gagctatact   1440
atgtgttccg gaaagtttag catcgacaaa gagatggcgg aaacgcaaca cggcacaacg   1500
gtcgtaaagg tgaagtacga gggtgcggga gcaccgtgta aagtcccaat tgagatcagg   1560
gatgtgaaca aggagaaagt ggtcggaaga gtgatctcgt ccacaccctt tgccgagaac   1620
acgaatagcg tcaccaatat cgagcttgaa ccccctttcg gagactcgta tatcgtcatt   1680
ggagtaggcg actcggcgtt gaccttgcac tggtttagaa aagggagcag catcggcaaa   1740
atgtttgagt caacatacag aggtgcgaag aggatggcga ttctcggaga gactgcgtgg   1800
gactttggtt cggtcggagg gctcctgaca tcccttggta aagcagtcca ccaggtgttc   1860
gggagcgtct acaccacgat gttcggaggt gtgtcatgga tggtgcggat tctcatcggg   1920
ttcttggtcc tttggatcgg aaccaattcg aggaatacat caatggcgat gacatgcatt   1980
gcggtcggtg gcatcacttt gtttctggga ttcaccgtac aggcataa                 2028
```